(12) United States Patent
Kishen

(10) Patent No.: US 9,987,200 B2
(45) Date of Patent: Jun. 5, 2018

(54) ACTIVATED MICRO-BUBBLE BASED ROOT CANAL DISINFECTION

(71) Applicant: Anil Kishen, Ontario (CA)

(72) Inventor: Anil Kishen, Ontario (CA)

(73) Assignee: SyACT, LLP, Plantation, FL (US)

( * ) Notice: Subject to any disclaimer, the term of this patent is extended or adjusted under 35 U.S.C. 154(b) by 318 days.

(21) Appl. No.: 14/477,682

(22) Filed: Sep. 4, 2014

(65) Prior Publication Data

US 2016/0067149 A1    Mar. 10, 2016

(51) Int. Cl.
| | |
|---|---|
| *A61K 6/00* | (2006.01) |
| *A61N 5/06* | (2006.01) |
| *A61M 37/00* | (2006.01) |
| *A61C 5/50* | (2017.01) |
| *A61N 5/067* | (2006.01) |

(52) U.S. Cl.
CPC .............. *A61K 6/0035* (2013.01); *A61C 5/50* (2017.02); *A61K 6/0017* (2013.01); *A61K 6/0052* (2013.01); *A61M 37/0092* (2013.01); *A61N 5/062* (2013.01); *A61N 5/0603* (2013.01); *A61N 5/0624* (2013.01); *A61N 2005/0606* (2013.01); *A61N 2005/067* (2013.01); *A61N 2005/0644* (2013.01); *A61N 2005/0651* (2013.01); *A61N 2005/0654* (2013.01)

(58) Field of Classification Search
CPC .. A61K 6/0035; A61K 6/0017; A61K 6/0052; A61C 5/04; A61C 5/50; A61M 37/0092; A61N 5/0603; A61N 5/062; A61N 5/0624; A61N 2005/0606; A61N 2005/0644; A61N 2005/0651; A61N 2005/0654

See application file for complete search history.

(56) References Cited

U.S. PATENT DOCUMENTS

| | | | |
|---|---|---|---|
| 7,261,561 B2 | 8/2007 | Ruddle et al. | |
| 7,306,459 B1 * | 12/2007 | Williams | ................. A61C 5/00 433/217.1 |
| 8,235,719 B2 | 8/2012 | Ruddle et al. | |
| 8,328,552 B2 | 12/2012 | Ruddle et al. | |
| 8,388,345 B2 | 3/2013 | Ruddle | |

(Continued)

OTHER PUBLICATIONS

International Search Report for PCT application PCT/US2015/047245 dated Nov. 27, 2015.

(Continued)

*Primary Examiner* — Cris L Rodriguez
*Assistant Examiner* — Hao D Mai
(74) *Attorney, Agent, or Firm* — Sandberg Phoenix

(57) ABSTRACT

A photo-chemically activated micro-bubble based root canal disinfection method for disinfecting a shaped root canal comprises (a) introducing a photoactive solution into the root canal, the photoactive solution containing a photoactive compound (such as methylene blue) dissolved in an alcohol carrier solution (such as polyethylene glycol and/or ethanol); (b) removing excess photoactive solution from the root canal; (c) introducing a micro-bubble solution comprised of an oxygen carrier (such as perfluorocarbon), an oxidizing agent (such as hydrogen peroxide) and a surfactant (such as a nonionic polyoxyethylene surfactant); (d) sonically or ultrasonically activating the micro-bubble solution in the canal; and (e) introducing light into the canal.

34 Claims, 25 Drawing Sheets

Basic Fluid dynamics in syringe irrigation

(56) References Cited

U.S. PATENT DOCUMENTS

| | | | |
|---|---|---|---|
| 2005/0182148 A1* | 8/2005 | Gaud | A61K 6/0017 |
| | | | 522/1 |
| 2006/0019220 A1 | 1/2006 | Loebel et al. | |
| 2007/0275353 A1* | 11/2007 | Gharib | A61C 5/04 |
| | | | 433/224 |
| 2008/0255498 A1* | 10/2008 | Houle | A61C 17/02 |
| | | | 604/20 |
| 2009/0130622 A1* | 5/2009 | Bollinger | A61C 1/0046 |
| | | | 433/29 |
| 2009/0220908 A1* | 9/2009 | Divito | A61C 5/02 |
| | | | 433/29 |
| 2009/0285766 A1 | 11/2009 | Kishen et al. | |
| 2010/0330539 A1* | 12/2010 | Glover | A61B 18/20 |
| | | | 433/224 |
| 2011/0027384 A1 | 2/2011 | Kishen et al. | |
| 2012/0237893 A1* | 9/2012 | Bergheim | A61C 5/02 |
| | | | 433/81 |
| 2012/0270177 A1* | 10/2012 | Nakashima | A61C 17/0202 |
| | | | 433/86 |
| 2013/0084544 A1* | 4/2013 | Boutoussov | A61M 31/00 |
| | | | 433/215 |
| 2013/0084545 A1* | 4/2013 | Netchitailo | A61C 5/02 |
| | | | 433/224 |
| 2014/0220505 A1* | 8/2014 | Khakpour | A61C 5/02 |
| | | | 433/81 |
| 2014/0342303 A1* | 11/2014 | Altshuler | A61C 17/0202 |
| | | | 433/29 |

OTHER PUBLICATIONS

Written Opinion of the International Search Authority for PCT application PCT/US2015/047245 dated Nov. 27, 2015.

Hamblin et al., Photodynamic Therapy: A New Antimicrobial Approach to Infectious Disease? Photochem. Photobiol. Sci., 2004, 3, pp. 436-450, The Royal Society of Chemistry and Owner Societies 2004.

Ochsner, Photophysical and Photobiological Processes in the Photodynamic Therapy of Tumours, Journal of Photochemistry and Photobiology B: Biology 39 (1997) pp. 1-18.

George et al., Photophysical, Photochemical, and Photobiological Characterization of Methylene Blue Formulations for Light-Activated Root Canal Disinfection, Journal of Biomedical Optics, May/Jun. 2007, vol. 12(3) (10 pages).

Jori et al., Photosensitized Inactivation of Microorganisms, Photochem. Photobiol. Sci., 2004, 3, pp. 403-405, The Royal Society of Chemistry and Owner Societies 2004.

Wainwright, Photodynamic Antimicrobial Chemotheraphy (PACT), Journal of Antimicrobial Chemotheraphy (1998) 42, pp. 13-28, The British Society for Antimicrobial Chemotherapy 1998.

George et al., Augmenting the Antibiofilm Efficacy of Advanced Noninvasive Light Activated Disinfection with Emulsified Oxidizer and Oxygen Carrier, JOE, vol. 34, No. 9, Sep. 2008, pp. 1119-1123.

Parsek et al., Bacterial Biofilms: An Emerging Link to Disease Pathogenesis, Annu. Rev. Microbiol. 2003, 57:677-701.

Costerton et al., Biofilms, The Customized Microniche, Journal of Bacteriology, 1994, 176(8):2137-2142, Journals.ASM.org.

De Gregorio, et al., Effect of EDTA, Sonic, and Ultrasonic Activation on the Penetration of Sodium Hypochlorite into Simulated Lateral Canals; An In Vitro Study, JOE, vol. 35, No. 6, Jun. 2009, pp. 891-895.

Eriksen, Has Caries Merely Been Postponed? Acta Odontol, Scand (1998), 56:173-175.

Wainwright et al., Methylene Blue—A Therapeutic Dye for All Seasons? Journal of Chemotherapy, vol. 14—n. 5, pp. 431-443 (2002).

O'Neill et al., Oral Bacteria in Multi-Species Biofilms Can be Killed by Red Light in the Presence of Toluidine Blue, Lasers in Surgery and Medicine, 31:86-90 (2002).

Triton X-100, Sigma Product Information Sheet (2 pages).

\* cited by examiner

George S, Kishen A. Augmenting antibiofilm efficacy of Advanced Non Invasive Light Activated disinfection. *Journal of Endodontics* 2008 Sep 34(9): 1119-23.

Sonically activated microbubbles
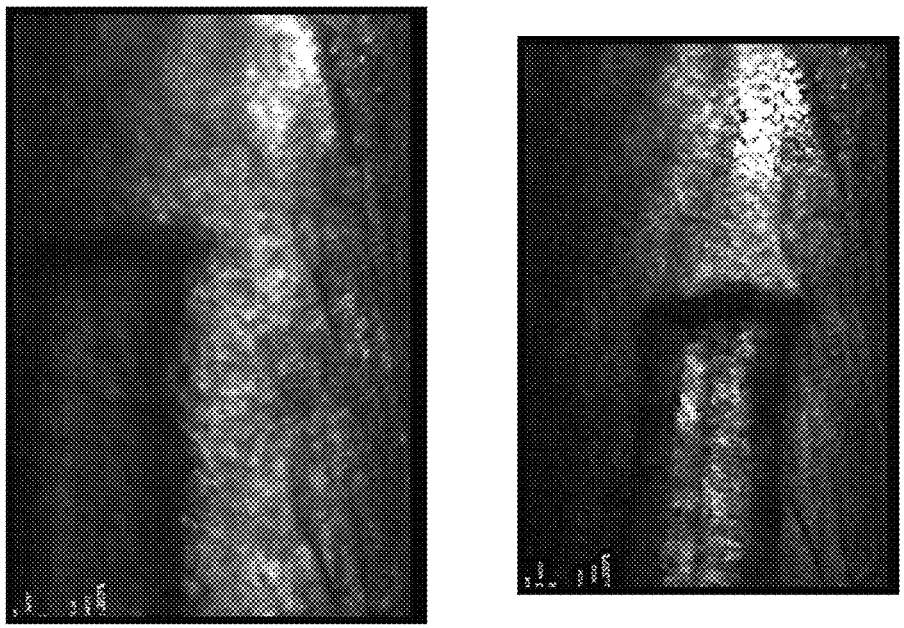
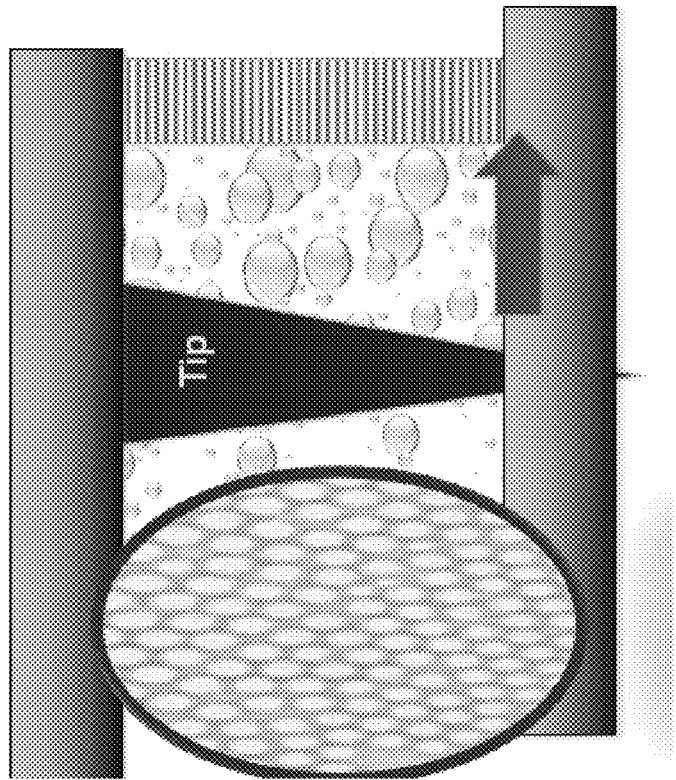
FIG. 10

A Kishen, S George, R Kumar. *J Biomed Mater Res A* 2006.

Group 3: PDT with MB in water (no activation)
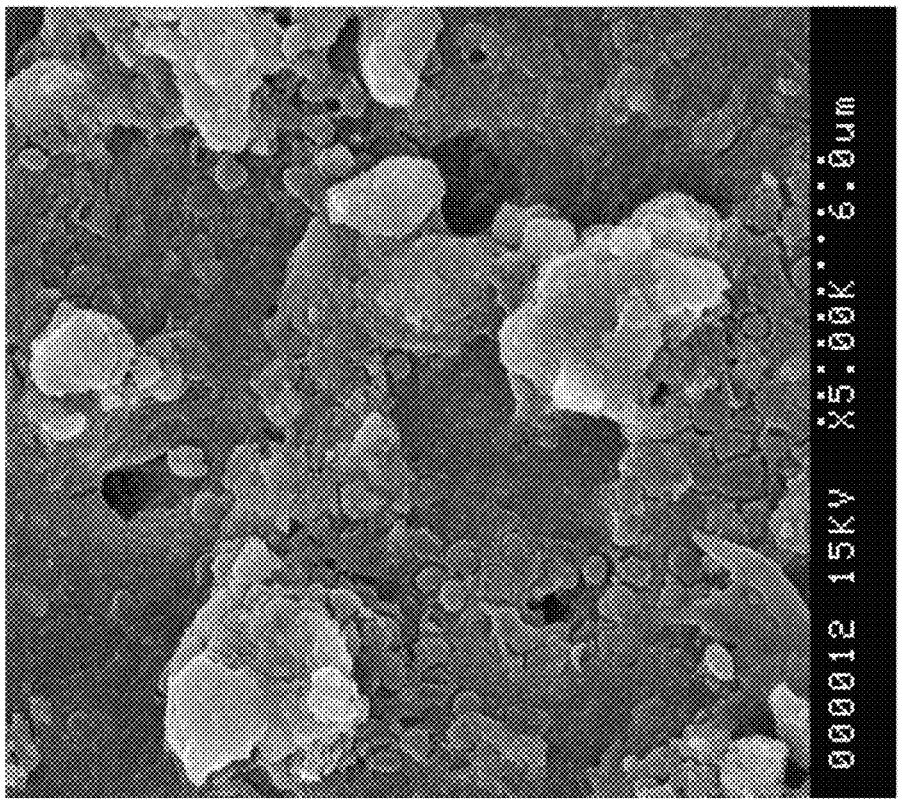
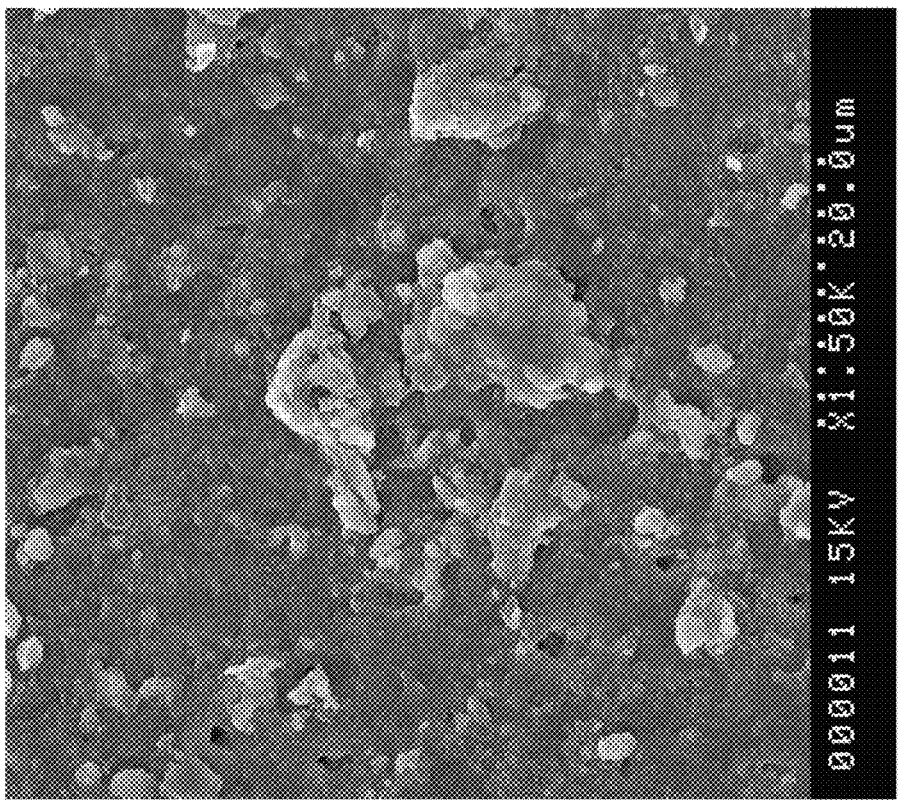
FIG. 17

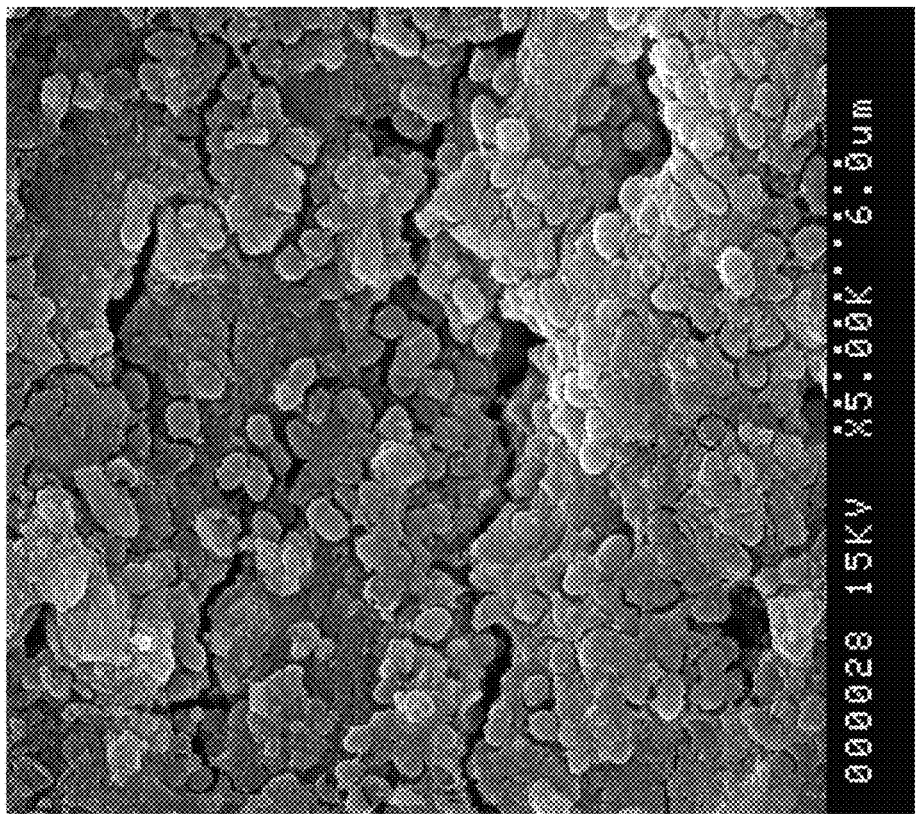
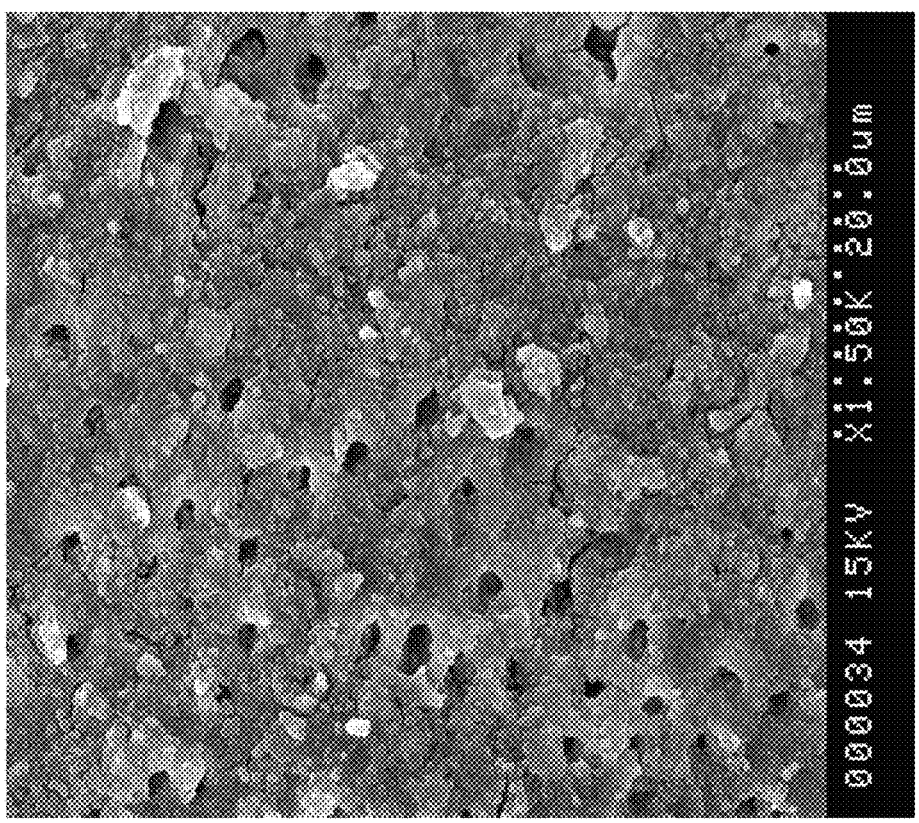
Group 3: Sonic activated PDT with MB in water
FIG. 18

PDT (photosensitizing compound in carrier solution) + microbubbles with activation

Synergized photo-chemically activated pulsating and propelling micro-bubble based root canal disinfection

| Bubble dynamics: Microbubble pulsation | Photodynamic therapy (PDT Potentiation 1) |
|---|---|
| Stable bubbles created at the tip of the EA during agitation pushes the microbubbles in the solution towards the root canal wall resulting in wall shear stresses to disrupt biofilm and remove debris | Light + Photosensitizer + Oxygen carrier + Oxidizer |
| Bubble dynamics: Microbubble chemical effect turbulence/propulsion) | Photodynamic therapy (PDT Potentiation 2) |
| Sonically/ultrasonically activated hydrogen peroxide in microbubbles will interact with the organic remnants in tooth. This will enhance the ability of microbubbles to debride the canal and facilitate microbubble turbulence/propulsion towards the wall | Light + Photosensitizer + sonic/ultrasonic energy |
| Bubble dynamics (Microbubble turbulence) | Photodynamic therapy (PDT Potentiation inside dentin tissue 3) |
| Stable bubbles created at the tip of the EA interacts with the microbubble in the solution to produced bubble coalescence, increasing fluid turbulence in the canal | Light is scattered by the microbubbles resulting better penetration of light energy into the dentin |

FIG. 23

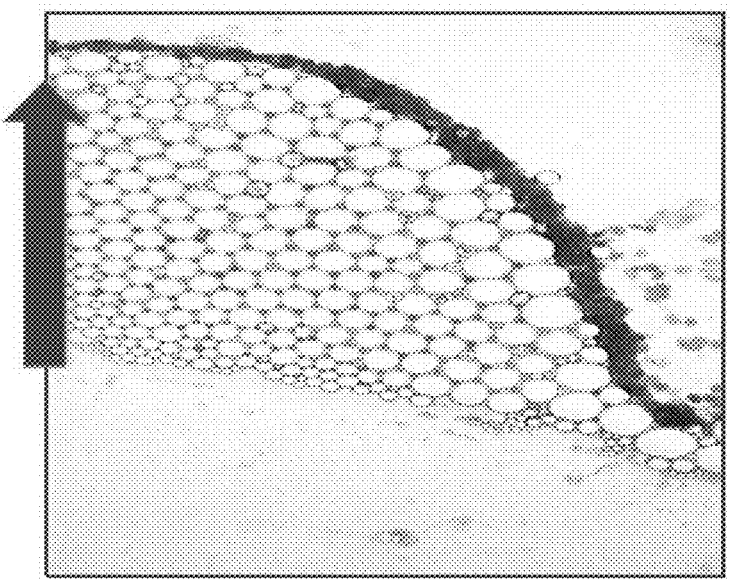
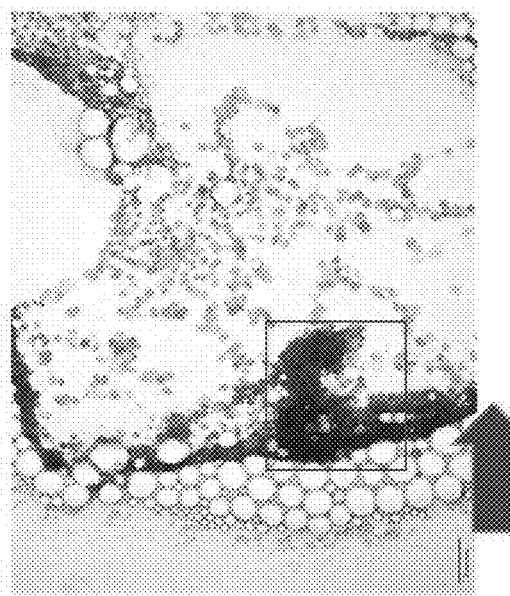
Coalescing and propelling microbubbles:
Upon interaction with organic remnants
Coalescing microbubbles within organic remnants
FIG. 24

ACTIVATED MICRO-BUBBLE BASED ROOT CANAL DISINFECTION

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

The present invention relates broadly to disinfection of root canals during endodontic, or root canal, procedures, and in particular to the use of micro-bubbles which when mechanically activated, for example, with ultrasonic/sonic energy improve the micro-bubble pulsations/interaction with the root canal wall (mechanical effect) and simultaneously enhance the efficacy of light activated disinfection (antibacterial effect).

Apical periodontitis is defined as an inflammatory process around the tooth root-apex, and is primarily a sequel to microbial infection (mainly bacteria) of the root-canal space of the tooth. Infection of the root canal and associated regions of tooth, generally known as root canal infection/endodontic infection, is a widespread problem all over the world. It represents a localized infection where bacteria have been recognized as the main etiological agent. The clinical manifestation of the disease is due to the combined action of microorganisms and host immune response.

The main objective of the clinical management of apical periodontitis (root canal infection) is to eliminate bacteria from the root canal system. If the periodontitis cannot be managed, the tooth will be lost and will need to be extracted. Traditional root canal treatment (RCT) aims to disinfect the root canal by removing the infected tissue and the disease causing bacteria by means of 'chemo-mechanical' preparation. Complete disinfection of the root canal is rarely achieved, although in most cases the disease symptoms recede.

There are several constraining factors in root canal disinfection. The first is the bacterial biofilm itself. The biofilm, comprised of bacteria and their products, covers the root canal wall and fills the dentinal microtubules. The biofilm (especially the biofilm in the microtubules) thus can be difficult to target chemically or to mechanically disrupt effectively. Chemicals, such as sodium hypochlorite are fairly effective at disinfecting the root canal. However, sodium hypochlorite can react with tissue remnants and the dentin in the canal, and can adversely affect the canal if left in the canal for too long. Thus, the longer duration required to effectively disinfect the canal must be weighed against the effect the sodium hypochlorite will have on the tooth structure. Other factors include the dentinal tubules, the dentin composition, and the complexities of the root canal structure itself.

The success rate of root canal treatment has generally been regarded as high, on the order of 87% (Eriksen H M, 1998). This figure applies to root canal treatment carried out by a specialist, where a higher expertise would result in a better technical standard of treatment, whereas the success rate in general practice is on the order of 72%. Failure of conventional treatment is mostly due to the persistence of bacterial population even after chemo-mechanical disinfection. Limitations in conventional treatment procedures are attributed to its inability to reach bacterial biofilm, especially in anatomically inaccessible regions of tooth. The presence of biofilms, which is the surface adsorbed growth of microorganism, has been associated with chronic human infections (Costerton J W et al, 1994; Parsek M R and Singh P K, 2003). This is because bacteria growing biofilms are highly resistant to conventionally used antimicrobial regimes, due to the biochemical composition of biofilm matrix and altered physiology of bacteria residing in biofilms (Parsek M R and Singh P K, 2003).

In traditional root canal therapy (RCT), the root canal is initially shaped by an instrumentation procedure (with root canal reamers and files) and then cleaned using root canal irrigants (liquid chemicals) and disinfected using medicaments to achieve a "bacteria free" root canal system. The chemicals most commonly employed for cleaning and disinfecting are sodium hypochlorite (NaClO), chlorhexidine (N,N''''1,6-Hexanediylbis[N'-(4-chlorophenyl)(imidodicarbon-imidic diamide)]) and EDTA, while calcium hydroxide (CaOH) is also used as an effective intra-canal medicament. These chemicals have to be supplemented with mechanical instrumentation to achieve bacterial elimination within the root canals. The primary limitation of current RCT methods is the inability of these chemicals to reach the anatomical complexities of the root canal.

Further, this method of bacterial elimination is not an instantaneous process and is found to be least effective in the anatomical complexities of the root canals. In the past, efforts were made to use higher concentrations of chemicals to achieve effective bacterial elimination. However, some of the perennial concerns were not examined. The effectiveness of these chemicals (such as root canal irrigants) at various depths inside the dentinal tubule is not clear. It has been demonstrated that the effective penetration of these chemicals into the dentinal tubules is limited, and therefore, bacteria remained viable at greater depths in the dentinal tubules at all levels in the root canal. Also, long-term use of such chemicals and medicaments can lead to the development of resistance to the chemicals and medicaments in the target organisms. Further, studies have shown that sodium hypochlorite reduces the modulus of elasticity and flexure strength of dentin structure, while saturated calcium hydroxide reduces the flexure strength of dentin. It has also been observed that some of the common root canal pathogens such as *Enterococcus faecalis* (*E. faecalis*) and *Candida albicans* (*C. albicans*) are resistant to calcium hydroxide.

Persistence of bacteria within the root canal dentin after root canal treatment is usually the main cause of failure of root canal treatment. Use of tetracycline has been found to effectively kill or destroy the bacteria. However, in most countries, tetracycline cannot be dispensed without a prescription. Thus, despite its effectiveness, the use of tetracycline was not a commercially viable option.

Recently, photodynamic therapy (PDT) has emerged as a promising treatment of cancer and other diseases utilizing activation of an external chemical agent, called a photosensitizer or PDT drug, by light. This drug is administered either intravenously or topically to the malignant site, as in the case of certain skin cancers. Subsequently, light of a specific wavelength, which can be absorbed by the PDT photosensitizer, is applied. The PDT drug absorbs this light producing a reactive oxygen species that can destroy the tumor. The photosensitizing compound is activated at a specific wavelength of light to destroy the target cell via a strong oxidizer, which causes cellular damage, membrane lysis and protein inactivation.

PDT relies on the greater affinity of the PDT drug for malignant cells. The light activation process of a PDT drug is initiated by the absorption of light to produce an excited singlet state (S1 or often written as 1P*, where P* represents the excited photosensitizer) which then populates a long-lived triplet state T1 (or 3P*) by intersystem crossing. It is the long-lived triplet state that predominantly generates the reactive oxygen species. Two types of processes have been proposed to produce reactive species that oxidize the cellular components (hence produce photooxidation) (Ochsner M, 1997).

Recent studies have shown that it is possible to kill bacteria, virus and fungi with low-power light/laser using the principles of photodynamic therapy (PDT) (Hamblin M R and Hasan T, 2004; O'Neill J F et al, 2002; Wainwright M, 1998; Jori G and Brown S B, 2004). PDT does not use a photothermal effect such as high powered lasers to eradicate bacteria. Therefore, PDT circumvents issues of thermal side effects in tissues. PDT has been used with relative success in the field of oncology for the treatment of neoplastic cells.

Different photosensitizers have been successfully demonstrated to have antibacterial property with their potential use in treating localized infections (Wainwright, M, 1998). Since the bactericidal activity of PDT is based on oxygen free radicals, the chance of microbes developing resistance is minimal compared to other strategies (Hamblin M R and Hasan T, 2004; Wainwright M and Crossley K B, 2004). Different photosensitizers have been successfully demonstrated to have antibacterial property with their potential use in treating localized infections (Wainwright M, 1998).

Since free radical generation is highly dependent on environmental conditions, the physicochemical environment existing at the site of application can influence the outcome of the treatment. Unlike the treatment of skin disease, the root canal has substantially no native oxygen. Hence, oxygen must be introduced into the root canal system. In US 2009/0287566 and US 2011/0027384, both of which are incorporated herein by reference, I described a more suitable photosensitizing composition that, as discussed below, can be further improved by either ultrasonic or sonic energy or agitation by increasing the rate of reactive oxygen release and subsequently the effectiveness of PDT. In addition, as discussed below, a micro-bubble solution, which is cationic or anionic, but preferable anionic, in nature, when activated with ultrasonic/sonic frequency or agitation will result in bubble (created by agitation)-bubble (in the solution) interaction and bubble-root canal wall interaction, which would facilitate the physical/mechanical effect of micro-bubbles. This physical/mechanical effect between micro-bubbles and root canal wall should significantly favor debridement and further enhance biofilm disruption. Meantime, an oxidizing agent (such as hydrogen peroxide) in the micro-bubble solution should interact with the organic debris within the root canal leading to the formation of oxygen, which allows the micro-bubbles to grow and propel towards the root canal wall (to further improve debridement). Finally, the presence of micro-bubbles in the solution should act as a scatterer, allowing light to penetrate laterally into the dentinal tubules/anatomical complexities of the root canal. Thus the solutions described therein appeared to provide excellent results in tests, a system for introducing the solutions into the root canal and activating the root canal is necessary.

BRIEF SUMMARY OF THE INVENTION

Briefly stated, my photo-chemically activated micro-bubble based root canal disinfection method comprises delivering a photosensitizing solution into a shaped canal. The photosensitizing solution comprises a photosensitizing compound dissolved in a carrier solution. The canal is flushed with, or otherwise exposed to, the photosensitizing solution for about 60 seconds to about 900 seconds, and preferably, for about 60 seconds to about 300 seconds, to allow the photosensitizing compound to penetrate dentin and uninstrumented areas of the canal. At the end of this period, excess photosensitizing solution is removed from the canal, for example, with paper points. The canal is then filled with a micro-bubble solution comprised of at least one oxygen carrier, at least one oxidizing agent, and at least one surfactant. The micro-bubble solution is mechanically activated, for example, sonically or ultrasonically, in the canal and light is introduced into the canal, for example, by means of a fiber optic cable sized to extend to the working end of the canal. The fiber optic cable can be sonically or ultrasonically energized such that it is the fiber optic cable that activates the micro-bubble solution. The illuminating tip of the fiber optic may be a bare fiber tip, or with modifications (diffuser, microlens) or may be tapered. After about 60 seconds to about 180 seconds of activation of the micro-bubble solution, and preferably after about 60 seconds to about 120 seconds, excess photosensitizing solution is removed from the canal, and the canal can then be sealed and obturated. The duration of light illumination will be standardized based on the dosimetry of light energy (10 J/cm$^2$ to 60 J/cm$^2$) achieved. In this case, the power of the light is inversely related to the duration of illumination. The light used for illumination can be any type of light. The light source can be, for example, a tungsten halogen light, a Light Emitting Diode (i.e., LED) or a laser. The wavelength of a laser, if a laser is used, corresponds to the absorption maxima of the employed photosensitizer (for example, Methylene blue (MB) is activated with a laser having a of wavelength 660 nm).

When the micro-bubble solution is mechanically activated, for example, sonically or ultrasonically, the micro-bubble solution releases oxygen bubbles. This rapid release of oxygen bubble and energy imparted to the micro-bubble solution by the sonic/ultrasonic activation markedly increases the rate of release of singlet oxygen, which in turn enhances the antimicrobial efficacy of photodynamic therapy. The sonic/ultrasonic activation of the micro-bubble solution in the root canal generates bubble/canal wall interactions throughout the axial length of the canal to mechanically disrupt the biofilm and canal debris. Additionally, the micro-bubbles scatter the light within the canal and introduce or otherwise direct light into the dentinal tubules and lateral canals, which would not otherwise be exposed to axially directed light. Thus, the light will reach, and be absorbed by, the photosensitizing compound, not only in the main canal, but also in dentinal tubules and lateral canals, and other areas, which would not otherwise be reached by axially directed light. As the photosensitizing compound absorbs the light, it is activated by the light, and the activated photosensitizing compound passes energy to the oxygen molecules, converting the oxygen molecules ($O_2$) to singlet oxygen (1P*). The singlet oxygen reacts with substances in the cells (i.e., in the bacteria) to destroy the cells. That is, the cells are destroyed by oxidative damage. The micro-bubbles in the solution will also interact with the micro-bubbles in the solution to produce stable bubbles exerting significant lateral wall shear stress to facilitate deeper penetration, significant debridement, and anti-biofilm ability.

In accordance with another aspect of the method, the method of disinfecting a shaped root canal comprises (a)

introducing a photoactive solution into the root canal, the photoactive solution containing a photoactive compound dissolved in an alcohol carrier solution; (b) removing excess photoactive solution from the root canal; (c) introducing a micro-bubble solution comprised of an oxygen carrier, an oxidizing agent and a surfactant; (d) sonically or ultrasonically activating the micro-bubble solution in the canal; and (e) introducing light into the canal. The steps (d) and (e) can be performed simultaneously.

The step of introducing the photoactive solution into the root canal can comprise flushing the root canal with the photoactive solution for at least 60 seconds. Preferably, the root canal is flushed with the photoactive solution for about 60 seconds to about 600 seconds, and preferably for about 60 seconds to about 180 seconds.

The step of mechanically activating the micro-bubble solution in the canal comprises mechanically activating the micro-bubble solution for at least about 60 seconds. Preferably, the micro-bubble solution is mechanically activated in the canal for about 60 seconds to about 180 seconds.

The light used to activate the photosensitive solution can be from a halogen lamp, an LED or a laser. If the light is from a laser, the laser is matched according to the photosensitizing compound used. Illustratively, the photoactive compound can be methylene blue, in which case, the laser operates at 660 nm.

The photoactive compound of the photoactive solution is chosen from the group consisting of toluidine blue (TBO), methylene blue (MB), rose bengal (RB) arianor steel blue, tryptan blue, crystal violet, azure blue cert, azure B chloride, azure 2, azure A chloride, azure B tetrafluoroborate, thionin, azure A eosinate, azure B eosinate, azure mix sicc, azure II eosinate, haematoporphyrin HCl, haematoporphyrin ester, aluminum disulphonated phthalocyanine, chlorins, photoactive fullerenes (e.g. CI6-b), aminolevulinic acid (ALA), bacteriochlorins, phthalocyanines, pheophorbides, purpurins, naphthalocyanines, indocyanine green, and combinations thereof. In a preferred embodiment, the photoactive compound is methylene blue or rose bengal arianor steel blue.

In accordance with one embodiment of the alcohol carrier solution, the alcohol carrier solution comprises polyethylene glycol and/or ethanol. In accordance with another embodiment, the alcohol carrier solution comprises polyethylene glycol, ethanol and water. In a preferred embodiment, the polyethylene glycol is glycerol. The polyethylene glycol, ethanol, and water are mixed in a ratio so that the final mixture has a refractive index close to that of dentin and at the same time had the ability to penetrate into the dentinal tubules. For example, the polyethylene glycol, ethanol, and water of the carrier solution can be combined in a ratio of about 1:1:1 to about 3:1:2. In another embodiment, the polyethylene glycol, ethanol, and water of the carrier solution are combined in a ratio of about 30:20:50 (or 3:2:5).

In accordance with one aspect of the photoactive solution, the photoactive compound has a concentration of about 2 micro molar to about 100 micro molar in the photoactive solution. In accordance with another aspect, the photoactive compound has a concentration of about 100 micro molar.

In accordance with an aspect of the micro-bubble solution, the oxygen carrier of the micro-bubble solution is chosen from the group consisting of perfluorodecahydro naphthalene, perfluorodecalin, perfluorohexane, octafluoropropane, perfluorobutane, perfluorooctane, perfluoromethyldecalin and $O_2IrCl(CO)P[C_6H_5]_3)_2$, and combinations thereof. In another aspect, the oxygen carrier of the micro-bubble solution is a perflourocarbon.

In accordance with an aspect of the micro-bubble solution, the oxidizing agent of the micro-bubble solution is chosen from the group consisting of hydrogen peroxide ($H_2O_2$), dilute sodium hypochlorite, dimethyl sulfoxide and chlorine dioxide and combinations thereof. In another aspect, the oxidizing agent of the micro-bubble solution is of hydrogen peroxide ($H_2O_2$). The concentration of the hydrogen peroxide ($H_2O_2$) used can about 3% to about 40% $H_2O_2$, and preferably about 35%.

In accordance with an aspect of the micro-bubble solution, the surfactant of the micro-bubble solution is chosen from the group consisting of mineral oil, glycerol, polyethylene glycol, non-ionic detergent, polypropylene glycol, SDS, a nonionic polyoxyethylene surfactant, cetrimide (an antibacterial detergent), and combinations thereof. In accordance with an further aspect, the surfactant of the micro-bubble solution is a nonionic polyoxyethylene surfactant.

The oxygen carrier, oxidizing agent and surfactant of the micro-bubble solution can be combined in a ratio of about 73:26.5:0.5 to about 75:24:1 by volume. In another aspect, the oxygen carrier, oxidizing agent and surfactant of the micro-bubble solution are combined in a ratio of 75:24.5:0.5 by volume.

BRIEF DESCRIPTION OF THE DRAWINGS

FIG. 7 is a graph showing the rate of singlet oxygen production in the micro-bubble solution with methylene blue dissolved in different ratios of perfluorocarbon (PFC), hydrogen peroxide, and water, wherein:

Figure 8:
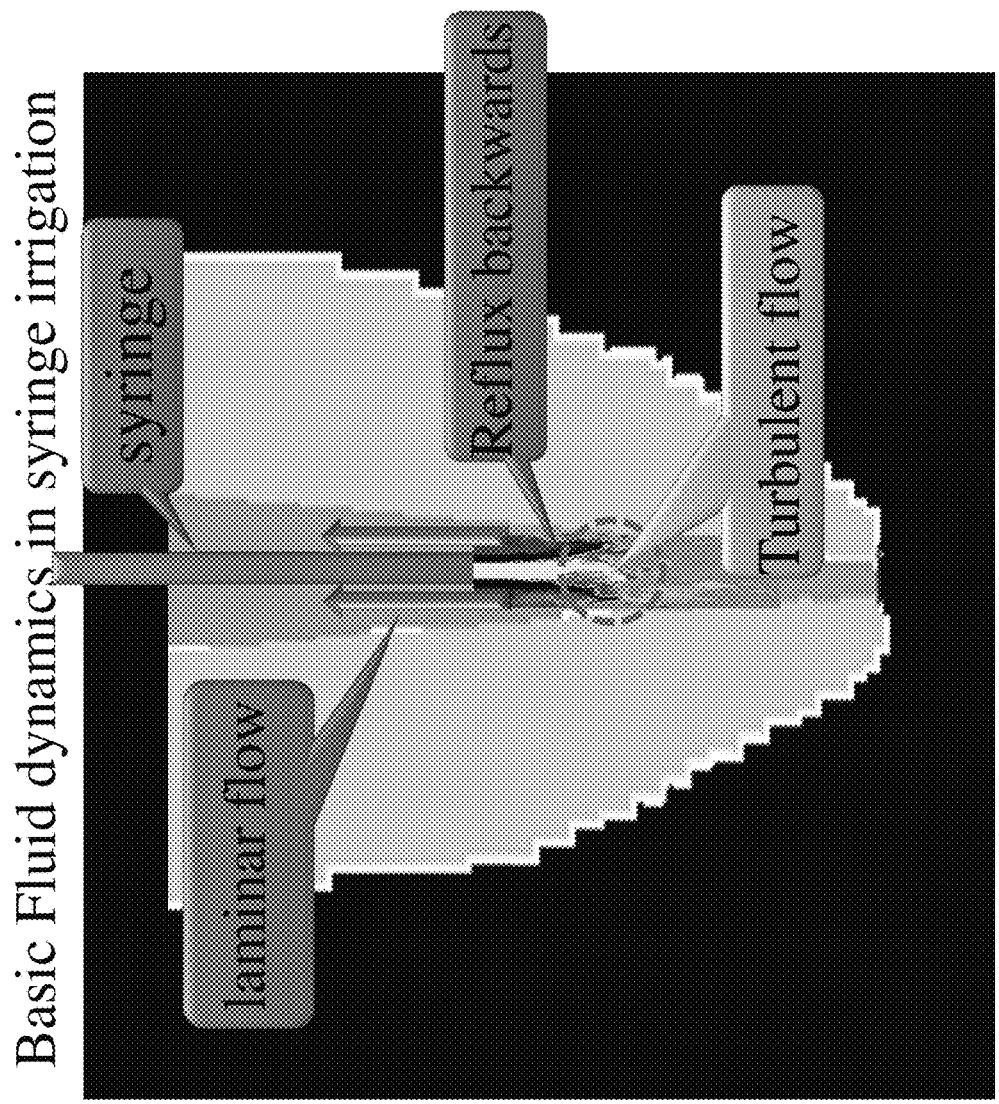
Figure 9:
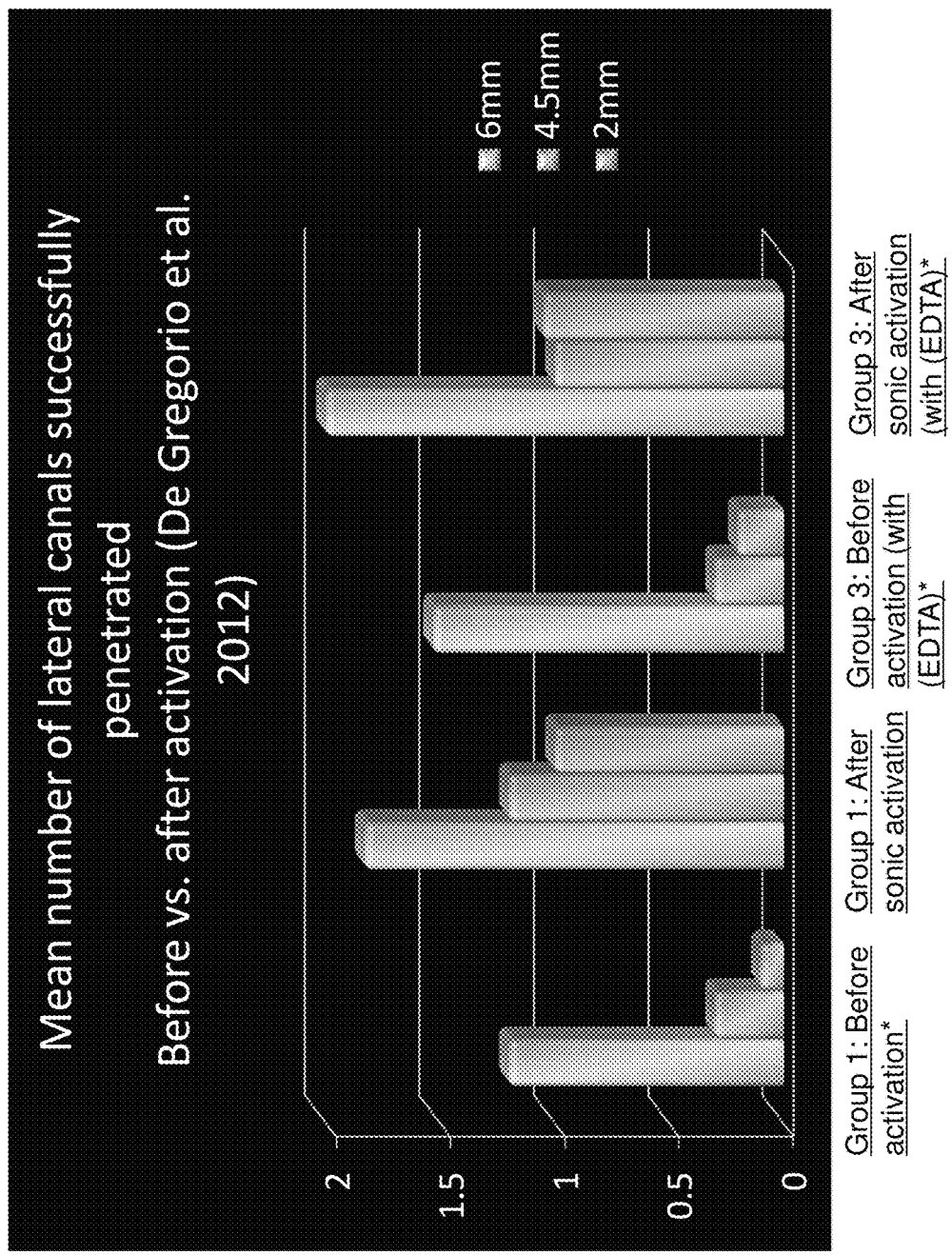
Figure 11:
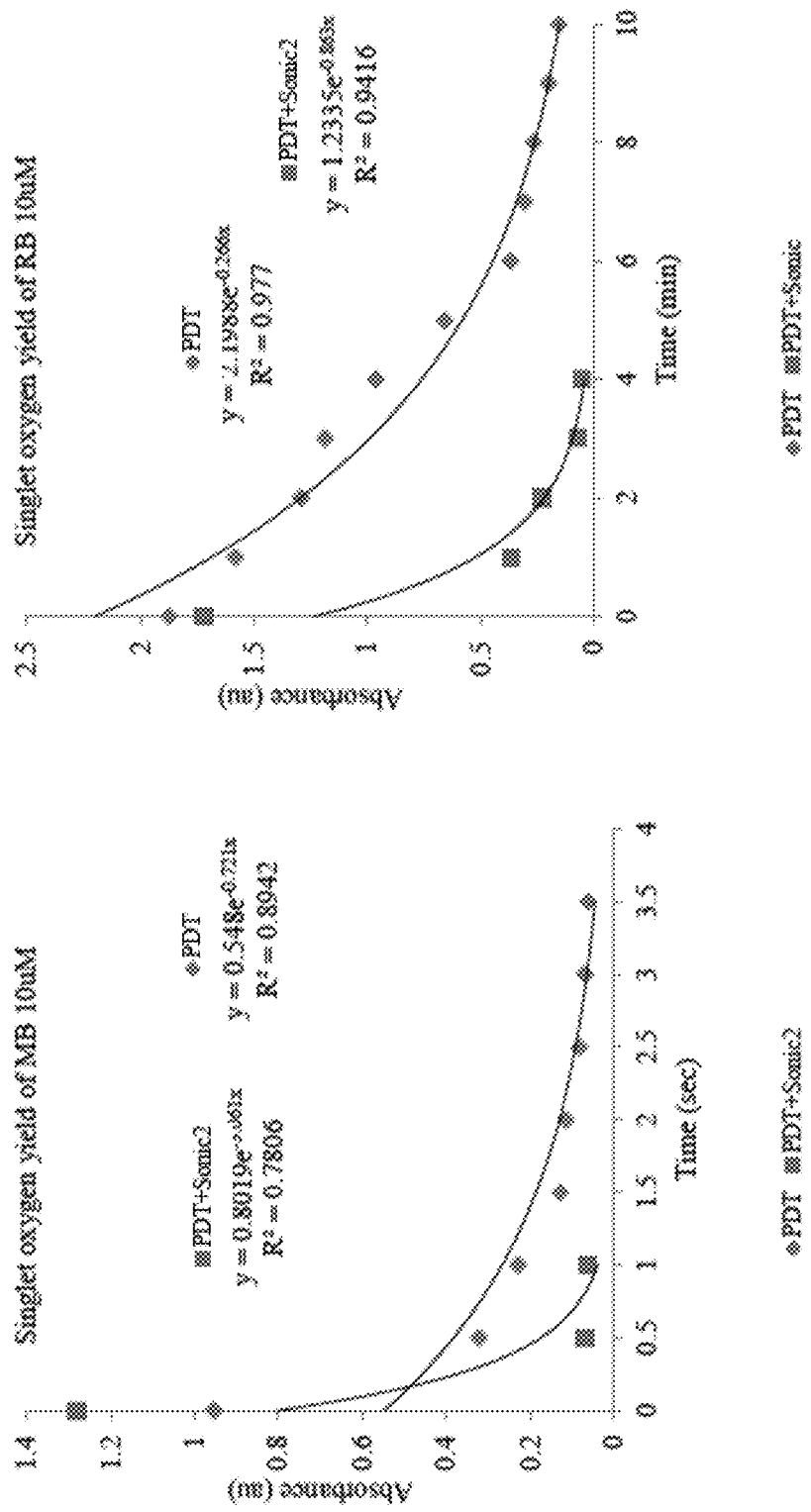
Figure 12:
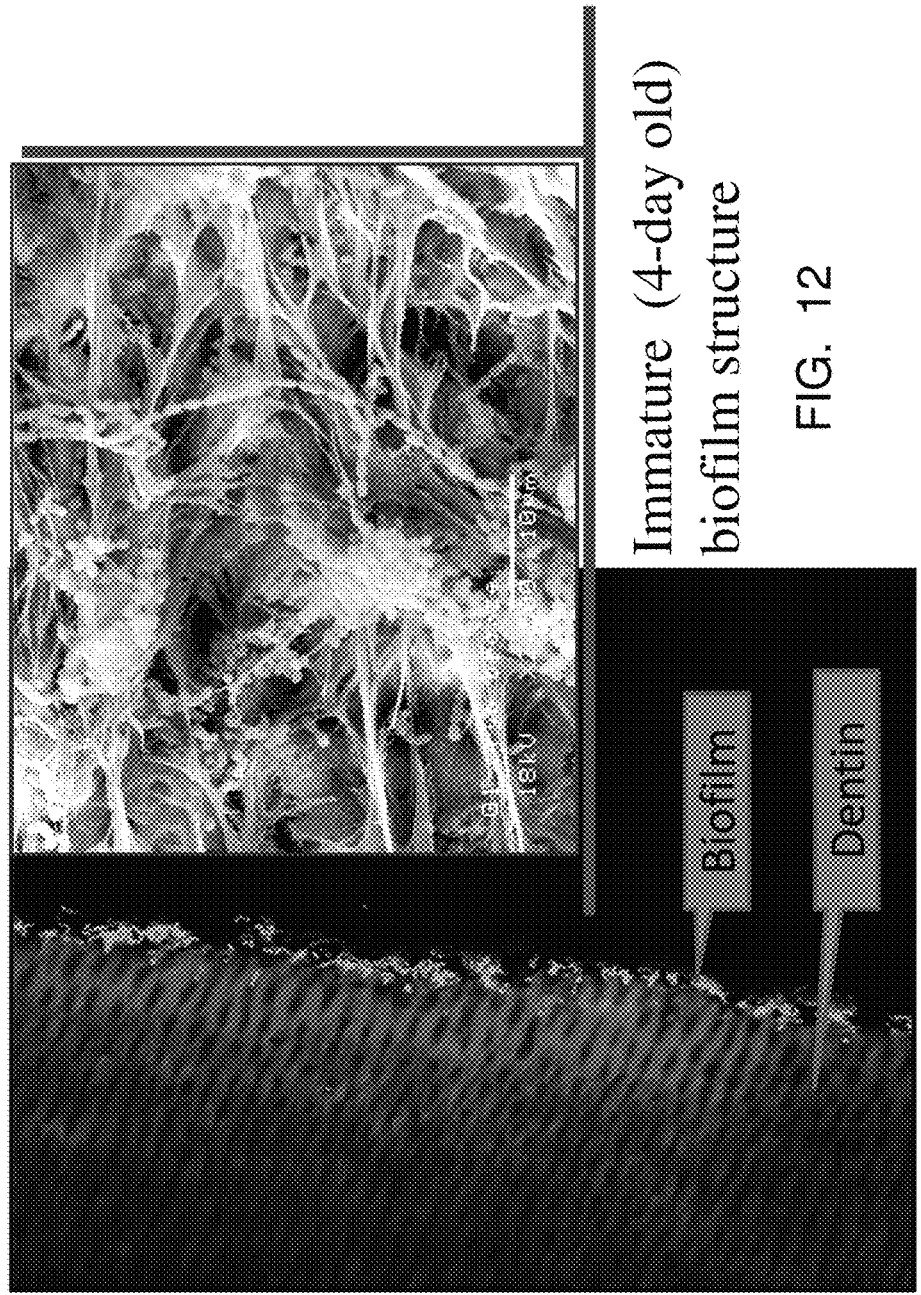
Figure 13:
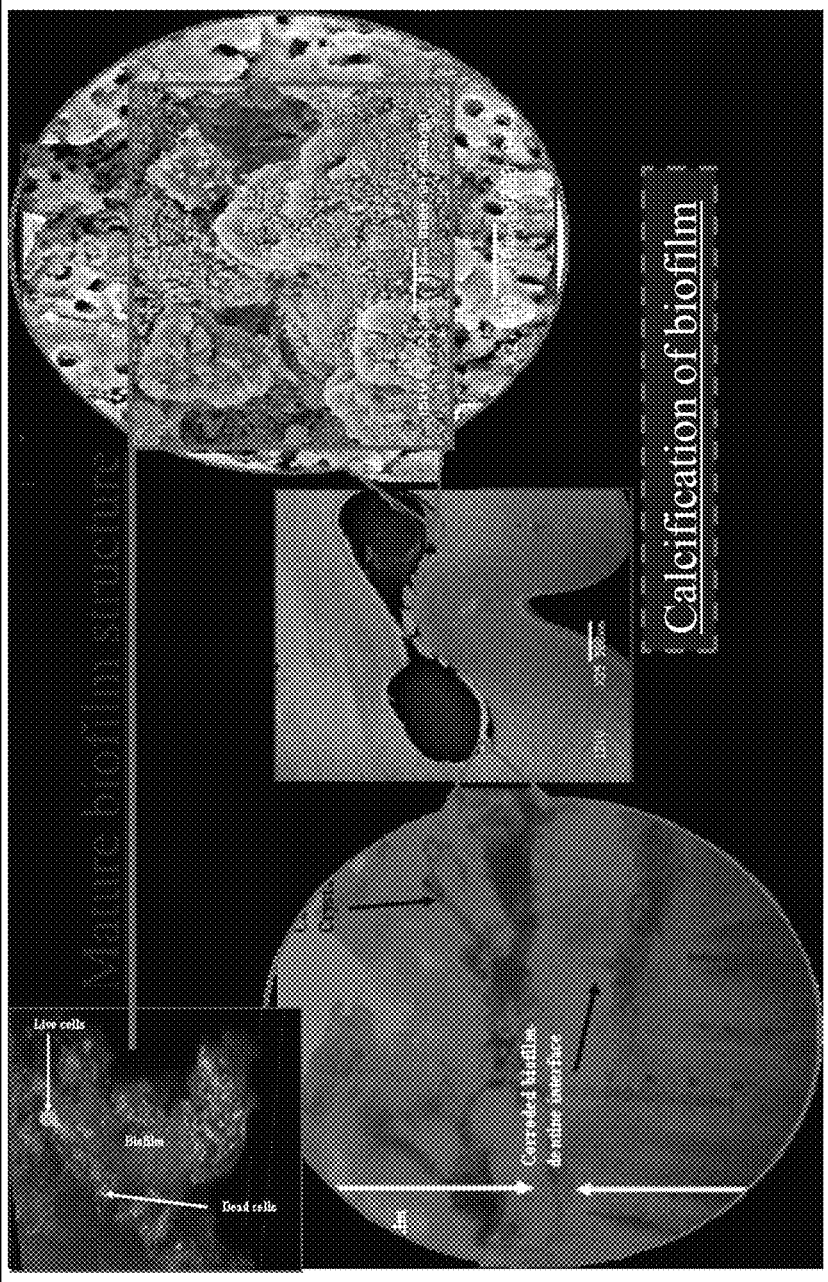
Figure 14:
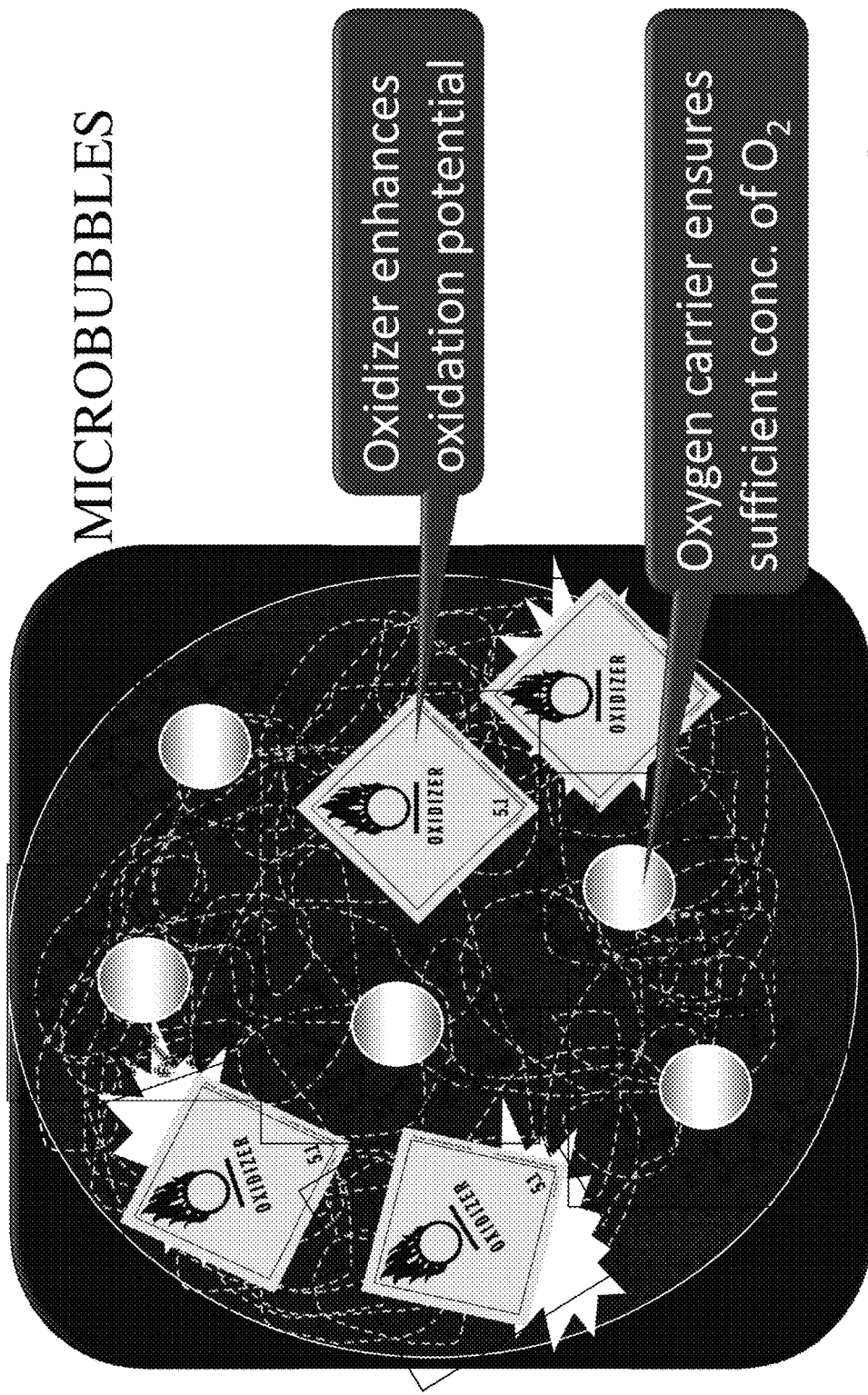
Figure 15:
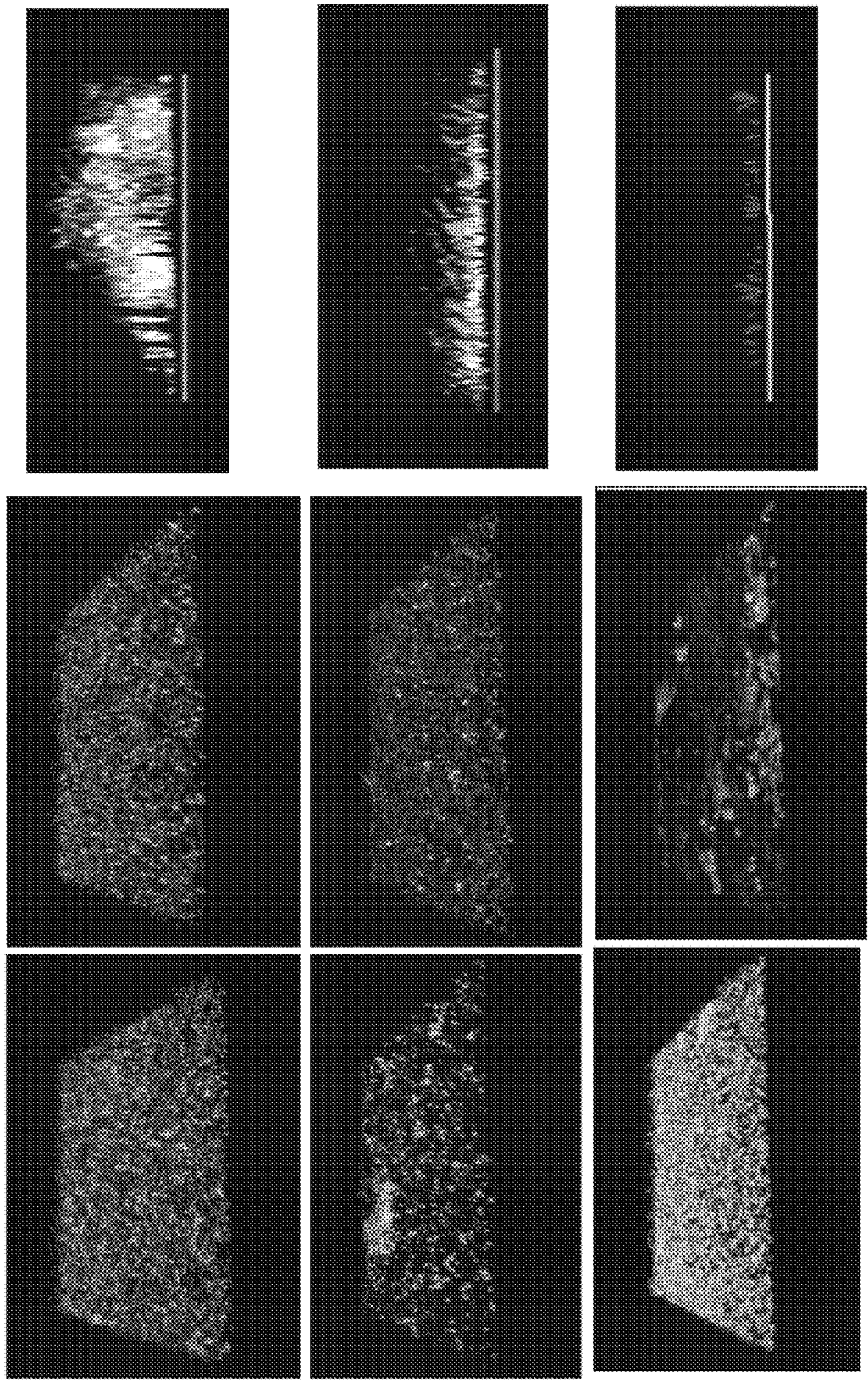
Figure 16:
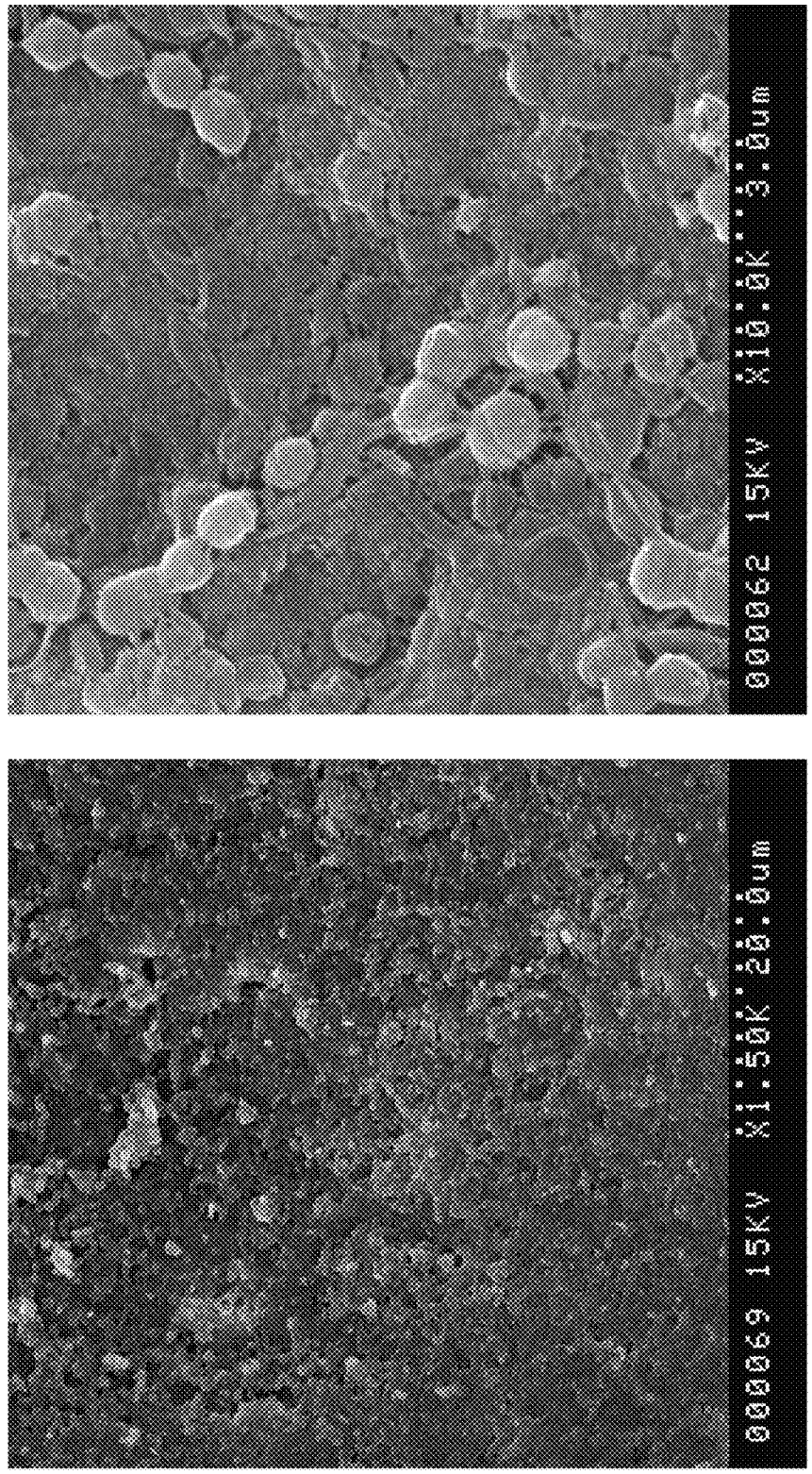
Figure 19:
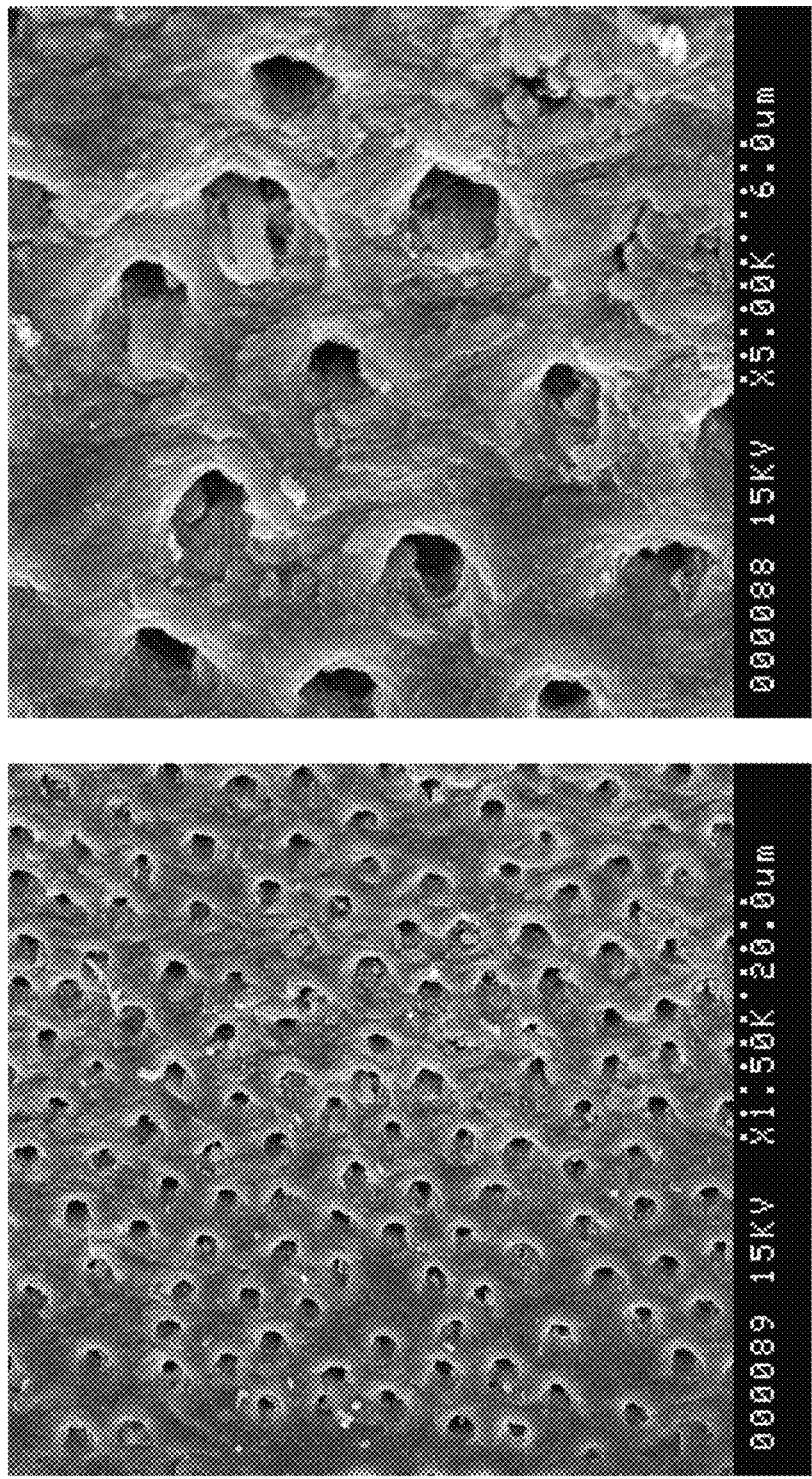
Figure 20:
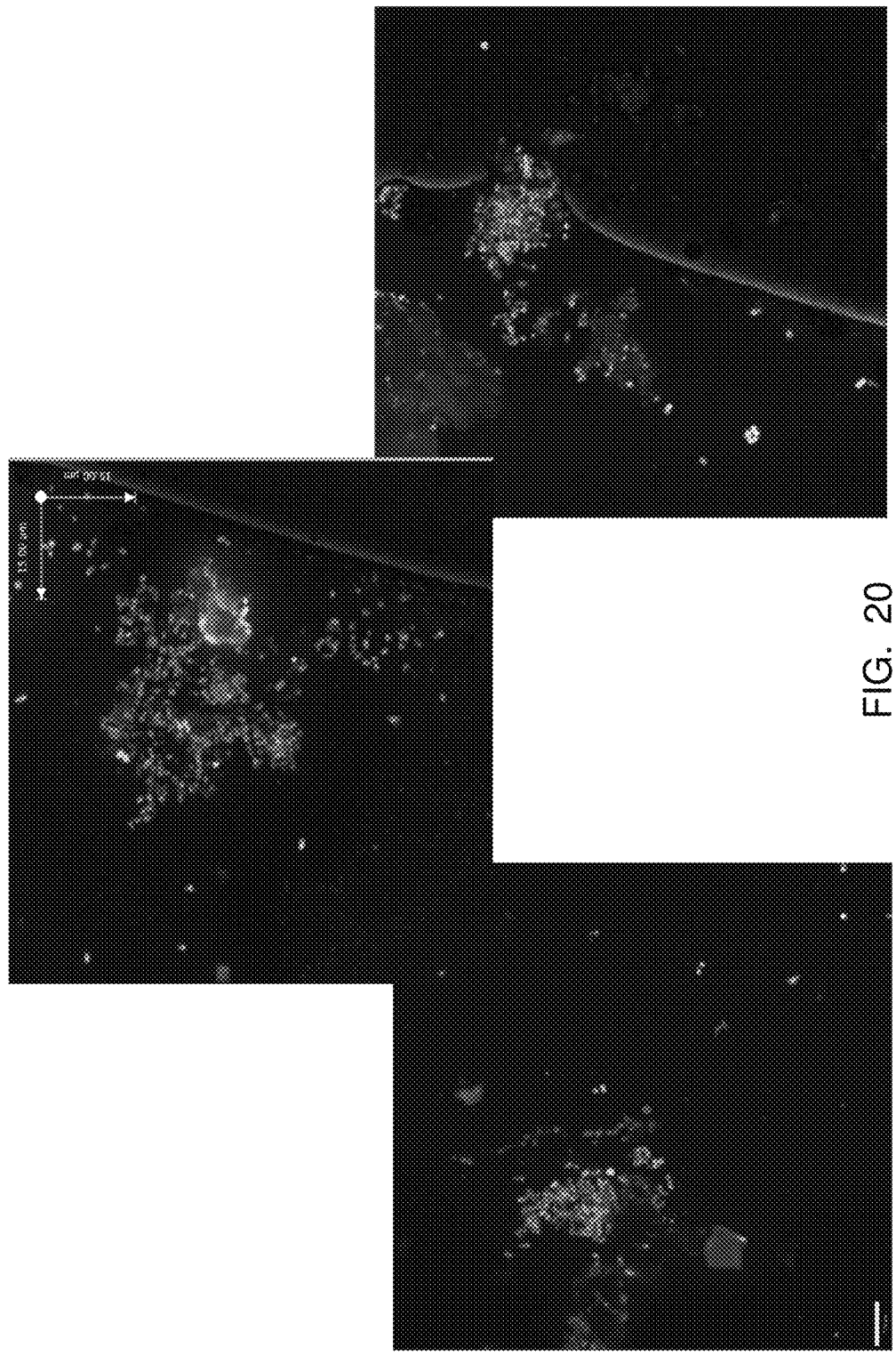
Figure 21:
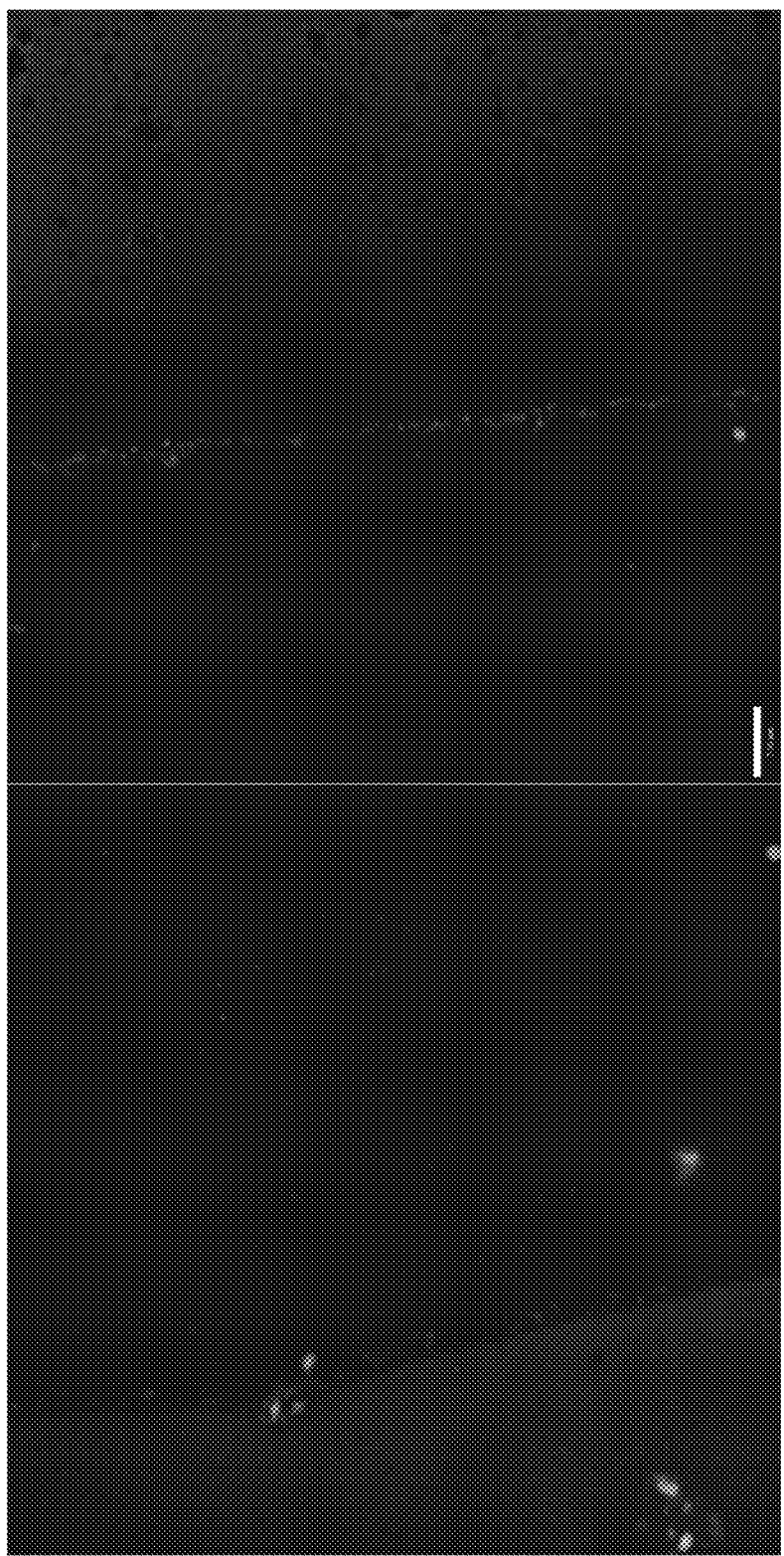
Figure 22:
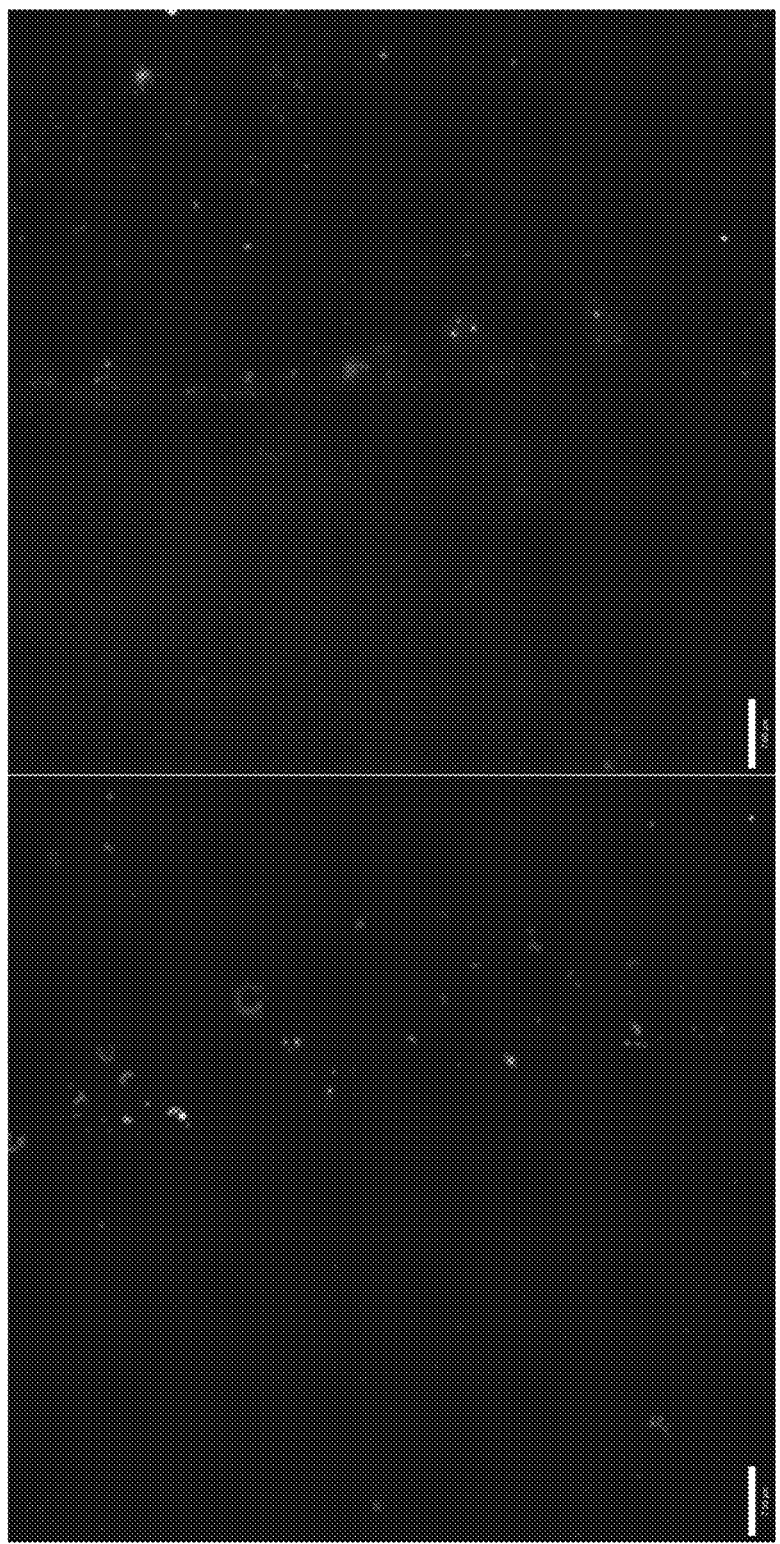
Figure 25:
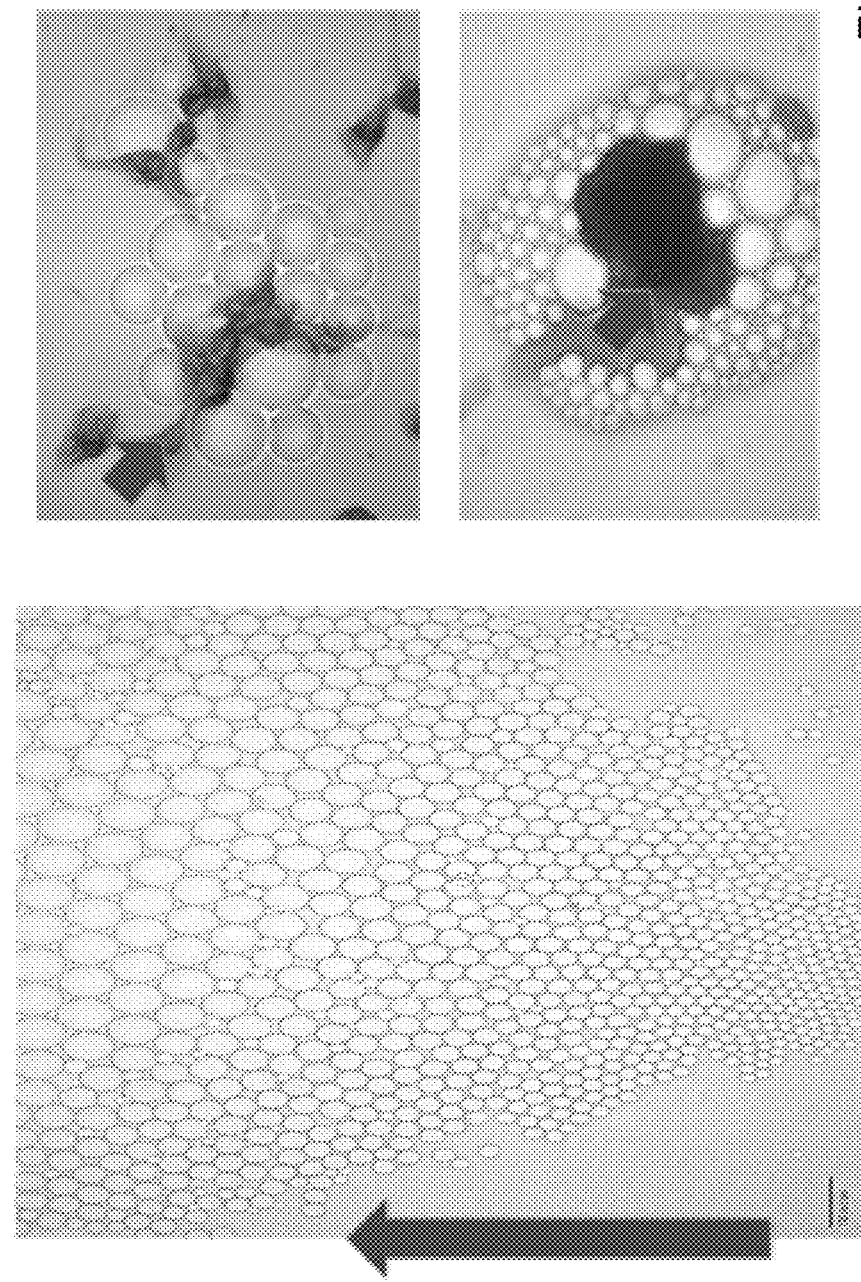

PF1 comprises 50 μmol/L of MB in combination with perfluorodecahydronaphthalene;

PF2 comprises 50 μmol/L of MB in combination with perfluorodecahydronaphthalene and $H_2O_2$ in a 66.6:33.3 ratio;

PF3 comprises, 50 μmol/L of MB in an emulsion produced by mixing perfluorodecahydronaphthalene:$H_2O_2$:Triton-X100 in a 60:35:5 ratio; and PF4 comprises 50 μmol/L of MB in an emulsion produced by mixing perfluoroecahydronaphthalene:$H_2O_2$:triton-X100 in a 75:24.5:0.5 ratio. PF-4 is demonstrated to produce maximum singlet oxygen release;

FIG. 8 is a schematic of fluid dynamics in a root canal when an antibacterial liquid (irrigant) is delivered using syringe irrigation;

FIG. 9 contains a graph showing the effect of fluid activation on the penetration of fluid into lateral canals of a root canal;

FIG. 10 contains photomicrographs (on the right) and a schematic drawing (on the left) showing the micro-bubbles that are produced in a root canal upon sonic/ultrasonic activation of the micro-bubble solution in the canal;

FIG. 11 contains graphs showing singlet oxygen yield of methylene blue (the left hand graph) and rose bengal (the right hand graph) both with and without sonic activation;

FIG. 12 contains a photomicrograph and colored cross-sectional photograph of immature (4-day old) biofilm on a root canal wall;

FIG. 13 contains images of a mature (6 week old) bio-film;

FIG. 14 is a schematic that graphically demonstrates the strategy of photoenhanced activated micro-bubble based root canal disinfection;

FIG. 15 contains in the first two columns, images showing the three-dimensional confocal laser scanning microscopy reconstruction of the *Enterococcus faecalis* biofilms subjected to different treatments (60×). The left column shows the biofilm receiving no treatment (top), methylene blue (photosensitizer) (100 µmol/L) treatment (middle) and PF4 micro-bubble solution treatment (bottom); the middle column shows the biofilm subjected to light (660 nm) irradiation alone (top), methylene blue+light (660 nm) irradiation (middle) and PF4 micro-bubble solution treatment+light (660 nm); and the right column shows the sagittal section of the treatment groups as described in the middle column MB;

FIG. 16 contains scanning electron photomicrographs of untreated root canals showing the biofilm on the root canal surface;

FIG. 17 contains scanning electron photomicrographs of root canals treated via conventional light activated disinfection (i.e., photoactivation of methylene blue dissolved in water) without activation; the remnant smear layer, debris and bacteria can be observed on the root canal walls;

FIG. 18 contains scanning electron photomicrographs of root canals treated via sonically activated PDT treatment after using the methylene blue dissolved in water;

FIG. 19 contains scanning electron photomicrographs of root canals treated via photoactivation of methylene blue in water, without use of the micro-bubble solution; although the smear layer and bacterial reduction was marginally better than the group of FIG. 17, the root canal wall still showed significant smear layer and adherent bacterial biofilm;

FIG. 20 contains scanning electron photomicrographs of root canals treated via photoactivation of methylene blue in water, ethanol and polyethylene glycol in the presence of activated micro-bubble solution; in these photomicrographs, the root canal surface is devoid of smear layer, debris and any biofilm structures;

FIGS. 21-22 show laser confocal microscopy images showing bacterial biofilms (and dead cells as red and viable cells are green). These images are of a root canal from a control group (i.e., untreated) (FIG. 21), a root canal disinfected via photoactivation of methylene blue in water in the presence of mechanically activated micro-bubble solution (FIG. 22);

FIG. 23 describes the different mechanisms of the micro-bubble solution for root canal disinfection. When mechanically activated, for example, with ultrasonic/sonic frequency agitation, the micro-bubble solution will activate different mechanisms in the root canal. (1) The bubbles generated by agitation of the liquid and the micro-bubbles in the solution interacting producing significant and bubble-root canal wall interaction, which should be responsible for the physical/mechanical effect of micro-bubbles on debridement and biofilm disruption; (2) The hydrogen peroxide in the micro-bubble solution should interact with the organic tissue debris within the root canal leading to the formation of oxygen, which causes the micro-bubbles to grow further and propel towards the root canal wall (the location of tissue remnants) to further improve debridement and antibiofilm effect as shown in FIGS. 24 and 25; and FIGS. 24 and 25 each comprise three images showing micro-bubbles being propelled toward the root canal surface and coalescing on the root canal surface.

Corresponding reference numerals will be used throughout the several figures of the drawings.

DETAILED DESCRIPTION OF THE INVENTION

The following detailed description illustrates the invention by way of example and not by way of limitation. This description will clearly enable one skilled in the art to make and use the claimed invention, and describes several embodiments, adaptations, variations, alternatives and uses of the claimed invention, including what I presently believe is the best mode of carrying out the claimed invention. Additionally, it is to be understood that the claimed invention is not limited in its application to the details of construction and the arrangements of components set forth in the following description or illustrated in the drawings. The claimed invention is capable of other embodiments and of being practiced or being carried out in various ways. Also, it is to be understood that the phraseology and terminology used herein is for the purpose of description and should not be regarded as limiting.

Figure 1:
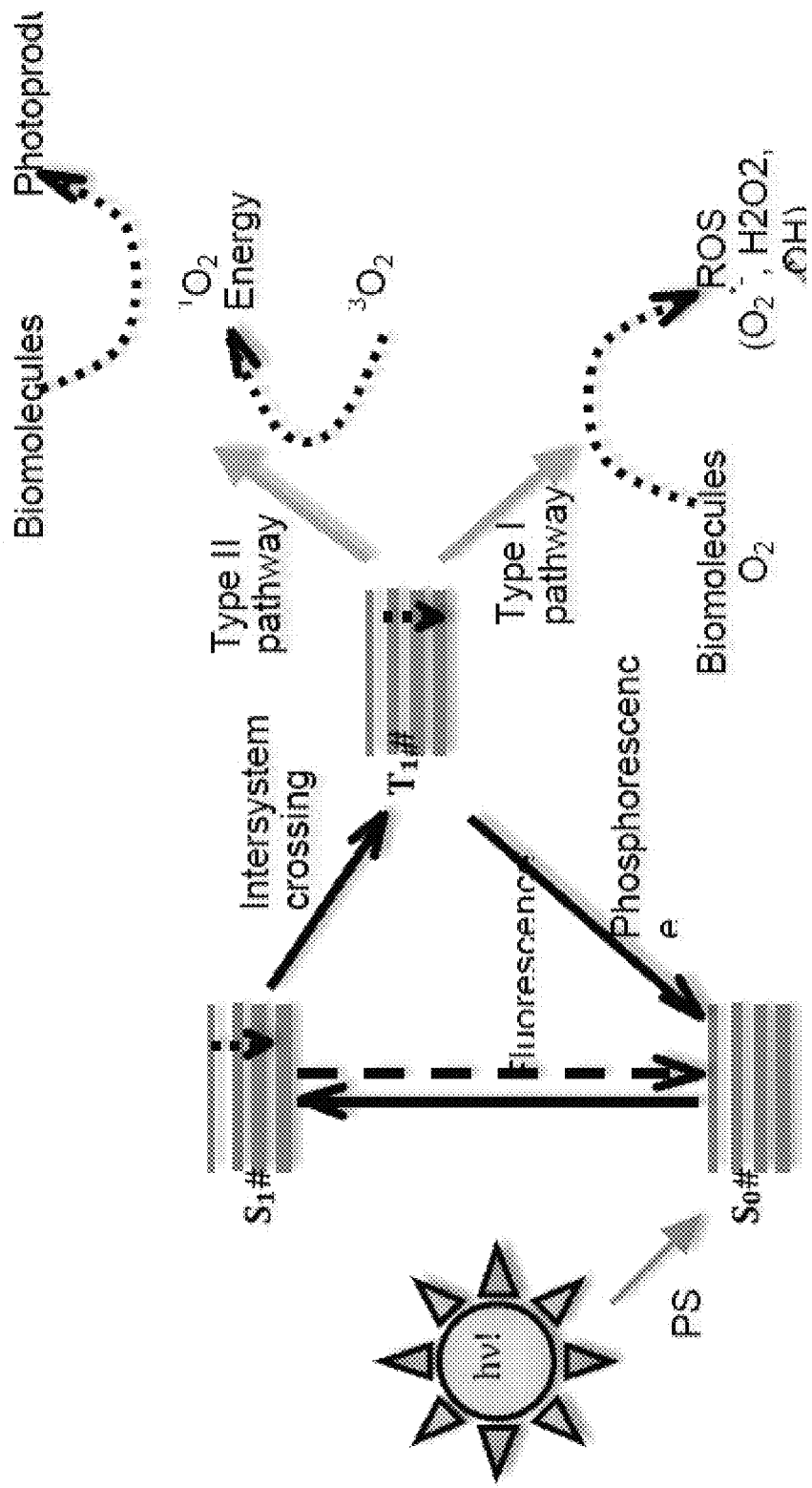
FIG. 1 is a schematic representation of root canal disinfection via photo-chemically activated micro-bubbles.

My disinfection method is shown schematically in FIG. 1. Briefly, the root canal disinfection method initially involves preparing and shaping the canal. This can be accomplished using conventional cleaning and shaping tools, such as files, reamers, etc. After the root canal has been shaped and cleaned, the canal is rinsed with a photosensitive solution, comprising a photosensitive compound dissolved in a carrier solution. The carrier solution enables the photosensitive compound to penetrate the dentin up to a distance of 1-2 mm, and the photosensitive compound will adhere to the biofilm and bacteria in the biofilm throughout the root canal system (including in microtubules). To facilitate penetration of the dentin by the photosensitive compound, the root canal is flushed with (rather than simply soaked in) the photosensitive solution. Flushing/application with the photosensitive solution can be for about 60-600 seconds, and preferably about 60 to about 300 seconds. Excess photosensitive solution is then removed from the canal using, for example, paper points. Importantly, after removal of the excess photosensitive solution, there is still a thin layer of photosensitizing solution in the canal that has bound to the canal surfaces and to the biofilms/tissue remnants in the canal.

Figure 3:
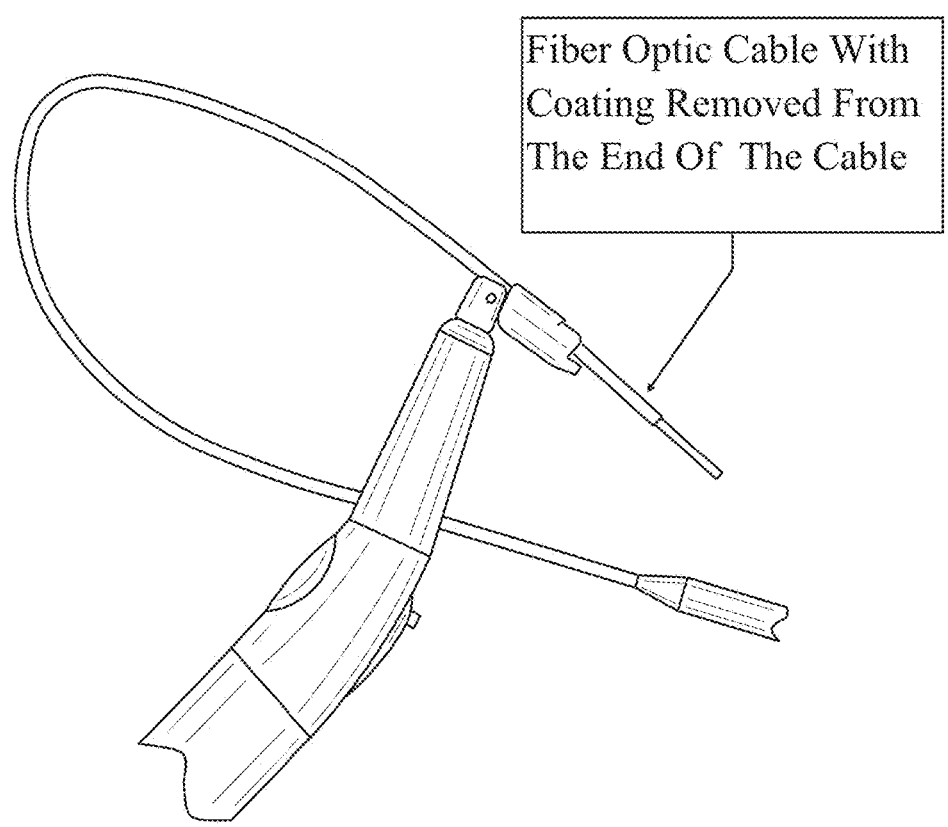
FIG. 3 is a photograph of a prototype activator used to both mechanically activate the micro-bubble solution and to introduce light into the root canal.

After excess photosensitizing solution has been withdrawn from the canal, the canal is filled with a micro-bubble solution which is comprised of an oxidizing agent, an oxygen carrier and a surfactant. The surfactant can be neutral, anionic or cationic. The micro-bubble solution is then mechanically activated (for example sonically or ultrasonically, in the canal, and light is introduced into the canal. For example, the solution can be mechanically activated using an EndoActivator® driver and tip which is available from Dentsply Tulsa Dental. Preferably, the tool used to mechanically activate the micro-bubble solution also introduces light into the canal to achieve ultrasonic/sonically activated photodynamic therapy. A prototype device is shown in FIG. 3 in which a fiber optic thread is secured to the head of an EndoActivator® driver to be sonically driven. Activation of the micro-bubble solution generates dissolved oxygen bubbles (and causes or induces acoustic microstreaming) in the canal. These bubbles will interact with and produce significant bubble/canal wall interaction (micro-bubbles bouncing from the walls of the canal), which mechanically disrupts the biofilm, and removes debris and smear layer from the root canal wall. Additionally, the micro-bubbles scatter the light introduced into the canal, so that the light does not merely pass axially through the canal. The light will impact, and activate, the photosensitive compound throughout the root canal system, including photosensitive compound that is adhered to biofilm and/or bacteria in dentinal tubules, lateral canals, etc. As shown schematically in FIG. 1, the activated photosensitive compound releases energy to the oxygen molecules, converting the oxygen molecules to singlet oxygen (S1 or 1P*). The singlet oxygen is highly reactive, and destroys the biofilm and bacteria via oxidative damage.

The micro-bubble solution can be mechanically activated in the canal for about 60 to about 600 seconds, and preferably about 60 to about 180 seconds. As will be discussed more fully below, this method disrupts and destroys the biofilm, resulting in a canal that is substantially free of biofilm, as shown in FIGS. 20 and 22. Additionally, as will be discussed below, the photosensitive compound reaches uninstrumented portions of the canal, and via the photochemically enhanced micro-bubble activated disinfection, destroys bacteria in these uninstrumented areas of the canal. This method thus has applicability to minimally invasive endodontic (MIE) procedures or treatment.

Photosensitive Solution

The photosensitive solution comprises a photosensitive compound, which is dissolved in a carrier solution. The photosensitive compound can be one or more of the following: toluidine blue (TBO), methylene blue (MB), rose bengal (RB), arianor steel blue, tryptan blue, crystal violet, azure blue cert, azure B chloride, azure 2, azure A chloride, azure B tetrafluoroborate, thionin, azure A eosinate, azure B eosinate, azure mix sicc, azure II eosinate, haematoporphyrin HCl, haematoporphyrin ester, aluminum disulphonated phthalocyanine, chlorins, photoactive fullerenes (e.g. CI6-b), aminolevulinic acid (ALA), bacteriochlorins, phthalocyanines, pheophorbides, purpurins, naphthalocyanines, indocyanine green, or mixtures thereof. A preferred photosensitive compound is methylene blue (MB).

The photosensitive solution is described in US 2011/0027384 and US 2009/0285766, both of which are incorporated herein by reference. The carrier solution in which the photosensitizing compound is dissolved can be water or it can be an alcohol solution. Alcohol solutions tend to enable the photosensitive compound to penetrate more deeply into the dentin, and hence, the carrier solution is preferably an alcohol solution. The alcohol solution can comprise polyethylene glycol and/or ethanol. In a preferred embodiment, the photosensitizing compound carrier solution comprises a polyethylene glycol, an ethanol and water. The polyethylene glycol can be glycerol. The polyethylene glycol, alcohol and water can be combined in a ratio of about 1:1:1 to about 3:1:2 by volume. In a preferred embodiment, the polyethylene glycol, alcohol and water are combined in a ratio of 30:20:50 (or 3:2:5) by volume. The ratio 30:20:50 by volume was arrived at by adding the refractive indices of the components so that the final mixture has a refractive index close to that of dentin and at the same time had the ability to penetrate into the dentinal tubules. These features help the polyethylene glycol, alcohol and water mixture achieve better antimicrobial PDT in dentin tissue.

The ethanol used to prepare the carrier solution can be about 30% to about 100% ethanol. Preferably, the ethanol is of a concentration which when mixed with the polyethylene glycol and water produces a mixture that is about 30% ethanol. The photosensitizing compound in the photosensitizing solution is present in a concentration of less than about 100 micro-molar, and preferably between about 2 micro-molar to about 100 micro-molar. When the concentration of the photosensitizing compound in the photosensitizing solution exceeded 100 micro molar, there was marked aggregation of the photosensitizing compound in the photosensitizing solution, which impaired photodynamic effect. However, the degree of singlet oxygen release is proportional to concentration or the photosensitizing compound. Hence, to maintain the singlet oxygen release as high as possible, the preferred concentration of photosensitizing compound in the photosensitizing solution is about 100 micro-molar. (George S, Kishen A., *Photophysical, photochemical, and photobiological characterization of methylene blue formulations for light-activated root canal disinfection*, J Biomed Opt. 2007 May-June; 12(3):034029.)

Figure 2:
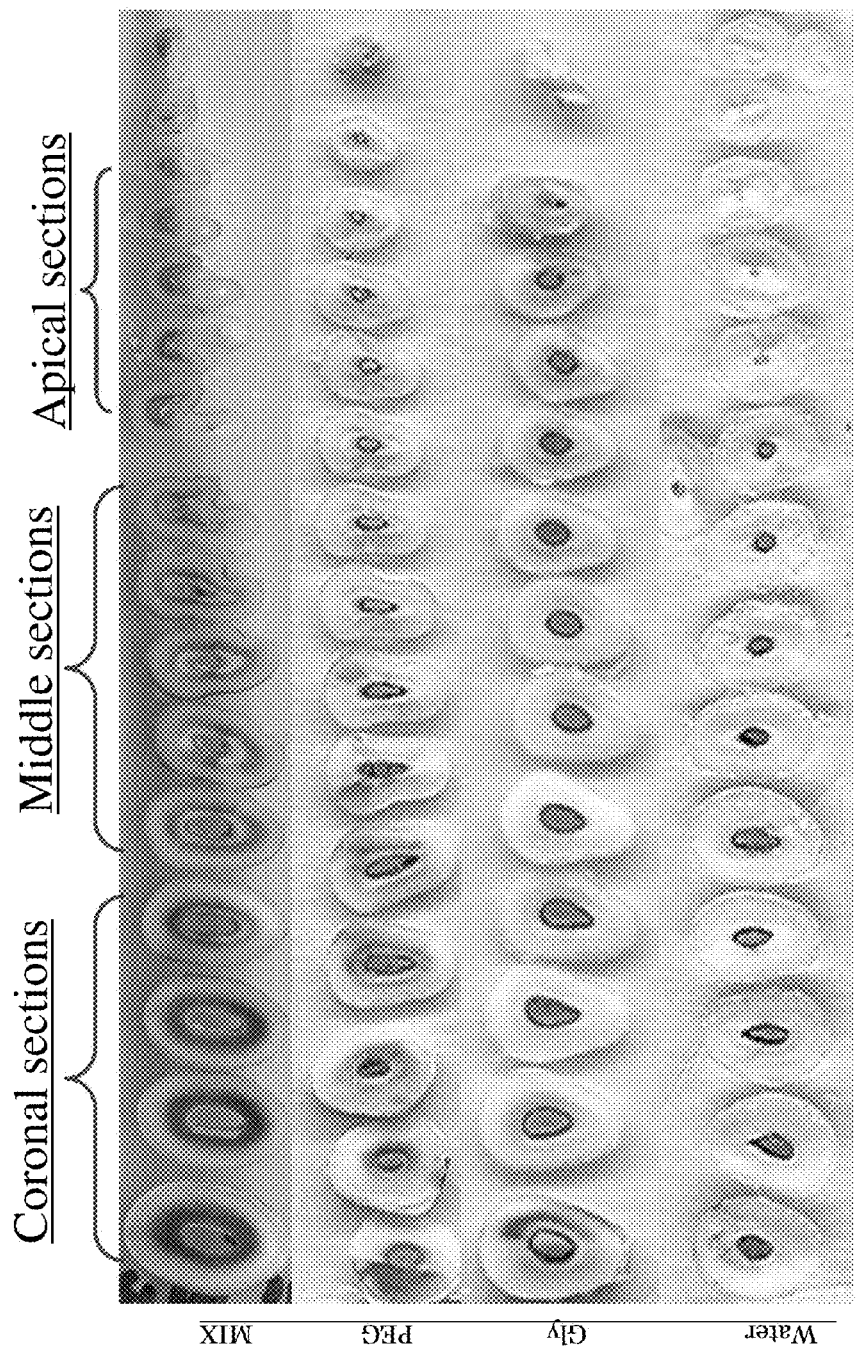
FIG. 2 contains photographs of tooth cross-sections showing diffusion into dentin of a photosensitizing compound (Methylene Blue) when dissolved in (1) water, (2) glycerol (GLY), (3) polyethylene glycol (PEG) and (4) a solution of water, glycerol and polyethylene glycol (MIX)

The carrier solution helps the photosensitizing compound better penetrate the dentinal tubules and anatomical complexities of the canal. It also aids in penetration of the photosensitizing compound into bacterial cells/biofilm structures. FIG. 2 shows a comparison of the penetration of different photosensitizing solutions as follows: (1) methylene blue (MB) in water, (2) MB in glycerol (Gly), (3) MB in polyethylene glycol (PEG), and (4) MB in a water/glycerol/PEG solution (MIX). In each of these four photosensitive solutions, the methylene blue was present in a concentration of 100 micro-molar.

As can be seen from FIG. 2, the MB had very little penetration into the dentin when mixed only in water. The penetration was better for Gly and PEG. However, as seen, the penetration of the MB into the dentin was substantially better when the MB was dissolved in the polyethylene glycol, ethanol and water mixture. In the PEG/ethanol/water carrier solution, the methylene blue penetrated up to 2 mm into the dentin. This substantial penetration of the photosensitizing compound into the dentin enables the photosensitizing compound to contact and adhere to biofilm deep with the anatomical complexities of the root canal. As will become more apparent, this is one of the features of my method that enables minimally invasive endodontics.

Micro-Bubble Solution

The micro-bubble solution is described in US 2011/0027384 and US 2009/0285766, both of which are incorporated herein by reference. Preferably, the micro-bubble solution comprises at least one oxygen carrier, at least one oxidizing agent and at least one surfactant.

The oxygen carrier can be one or more of the following: perfluorodecahydro naphthalene, perfluorodecalin, perfluorohexane, octafluoropropane, perfluorobutane, perfluorooctane, perfluoromethyldecalin and $O_2IrCl(CO)P[C_6H_5]_3)_2$. The preferred oxygen carrier is a perfluorocarbon (PFC).

The oxidizing agent can be one or more of the following: hydrogen peroxide ($H_2O_2$), dilute sodium hypochlorite, dimethyl sulfoxide (DMSO) and chlorine dioxide. The preferred oxidizing agent is hydrogen peroxide ($H_2O_2$).

The surfactant can be one or more of the following: mineral oil, glycerol, polyethylene glycol, non-ionic detergent, polypropylene glycol, sodium dodecyl sulfate (SDS), a nonionic polyoxyethylene surfactant (such as Triton™ X or Triton™ X-100), or an antibacterial detergent (such as cetrimide, a mixture of different quaternary ammonium salts including Cetrimonium bromide). In particular, the nonionic detergent may be Triton™ X, and even more preferably, Triton™ X-100 (available from Sigma-Aldrich). Triton X-100 is a nonionic polyoxyethylene surfactant, having a specific gravity of 1.065 at 25° C. (about 1.07 g/mL), an approximate molecular weight of 625 (giving an effective molarity of 1.7 M for the neat liquid), a UV absorption of lambda max=275 nm and 283 nm in methanol, a viscosity (Brookfield): 240 cps at 25° C., a pH (5% aqueous solution) of 6.0 to 8.0, and critical micelle concentration (CMC) of 0.22 to 0.24 mM. It is soluble in all proportions at 25° C. in water, benzene, toluene, xylene, trichloroethylene, ethylene glycol, ethyl ether, ethanol, isopropanol, and ethylene dichloride. Triton X-100 has the following formula:

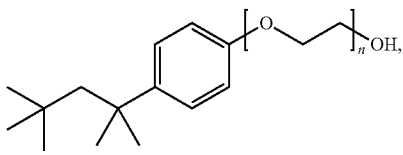

where n is about 9.5

The oxygen carrier, oxidizing agent and surfactant are combined in a ratio of about 60:35:5 to about 75:24.5:0.5 by volume. In a preferred embodiment, the oxygen carrier, oxidizing agent and surfactant are combined in a ratio of 75.0:24.5:0.5 by volume.

Micro-bubbles released from the micro-bubble solution are anionic, gas-filled bubbles having a size of about 2-4 microns. The gas core of the micro-bubbles contains most of the unit volume. Micro-bubbles in aqueous media are inherently unstable owing to surface tension effects, and therefore require a stabilizing shell. The surfactant of the carrier solution thus serves to stabilize the micro-bubbles.

Activation of the Micro-Bubble Solution

The micro-bubble solution, as noted above, is mechanically activated, for example, either sonically or ultrasonically. in the prepared tooth root canal. Additionally, as the micro-bubble solution is being agitated, light is introduced into the canal, for example, by means of a fiber optic cable. In fact, the fiber optic cable can be sonically or ultrasonically driven in the root canal. Light can be delivered into the canal using a fiber optic cable, and the light source can be an LED, a laser, or other light source. Preferably, the light source is a laser. The source (type) of the laser depends upon the type of photosensitizer used in the micro-bubble solution. In tests, methylene blue was used as a photosensitizer, hence the light source wavelength was 660 nm. The power of the laser tested ranged from 22 mW to 100 mW. Since the effectiveness of photodynamic effect depends on the dose of light, which is directly related to the power of the light source and duration of illumination, for a lower power source, longer duration of illumination can be used. Light doses ranging from 2 $J/cm^2$ to 60 $J/cm^2$ for about 60 to about 180 seconds was tested. Preferably, the fiber optic cable has no coating at the end which is received in the root canal to enable light to escape from the cable both through the sides (radially) and from the end (axially) of the cable. Such fiber optic cables are shown, for example, in FIGS. 3 and 4. FIG. 5C schematically shows light escaping from the fiber optic cable both axially and radially. As can be appreciated, the fiber optic cable is sized to extend to the working end of the prepared root canal, and thus has a diameter of about 0.5 mm or less.

Figure 4:
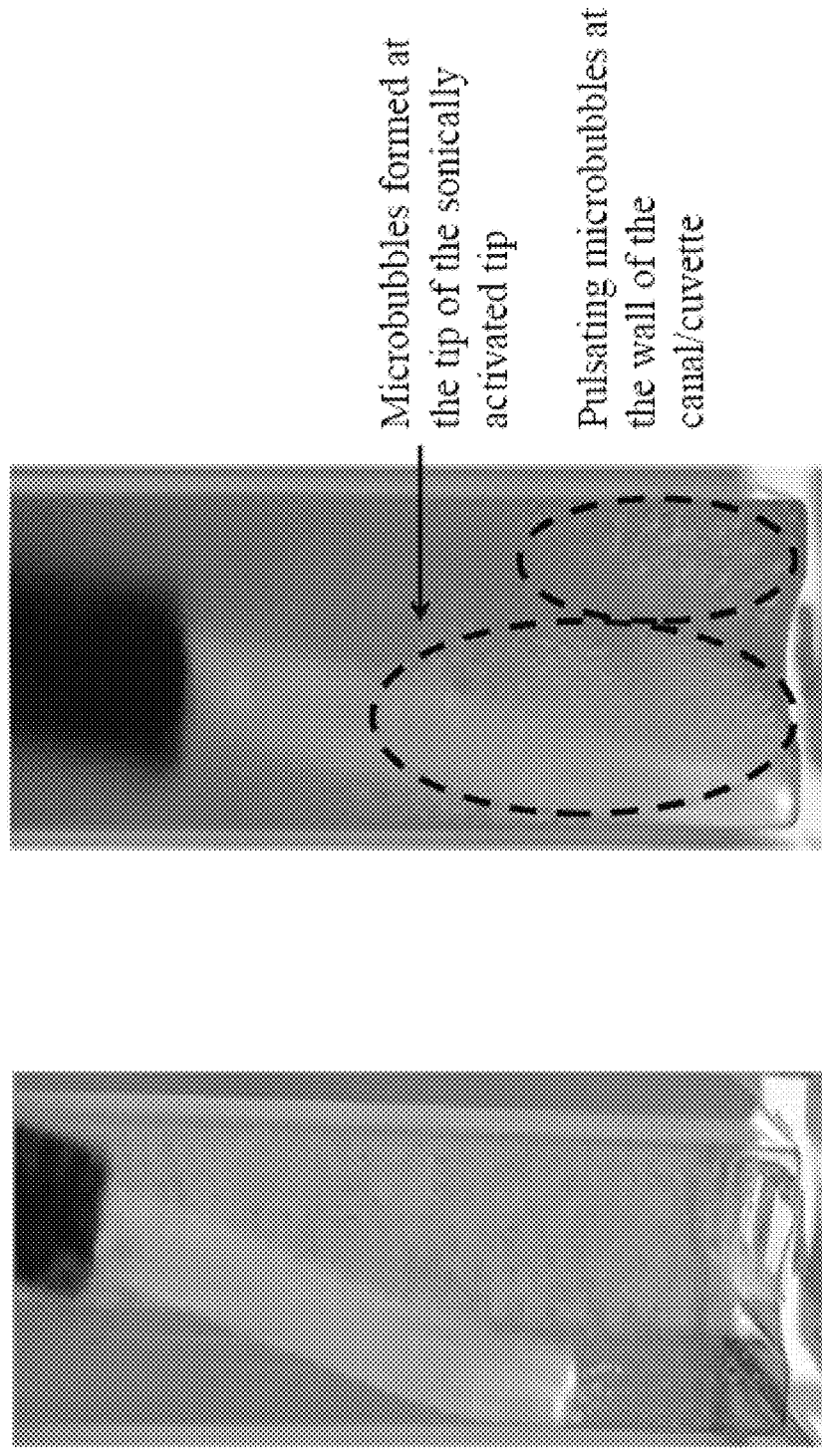
FIG. 4 contains enlarged photographs of the fiber optic activator in the micro-bubble solution in an unactivated state (left side) and in an activated state (right side)

In a preferred method, the fiber optic cable is used to mechanically activate the micro-bubble solution. In FIG. 3, the fiber optic cable is mounted to an irrigant activator, such as an EndoActivator® driver (available from Dentsply Tulsa Dental), and which is described in U.S. Pat. Nos. 7,261,561, 8,235,719, 8,328,552, and 8,388,345 all of which are incorporated herein by reference. This modified EndoActivator® driver was used in the testing of my method. FIG. 4 shows, on the right, sonic activation of the micro-bubble solution in a clear vial using a fiber optic cable in which the end of the cable is not coated (i.e., is stripped of its coating). The left hand picture shows the fiber optic cable in the micro-bubble solution. The light emanating from the cable can be seen to be picked up by the micro bubbles. As can also be seen in the left hand picture, there is little to no activity in the solution. The right hand picture shows the fiber optic cable sonically activating the micro-bubble solution. A high degree of activity is shown around the tip of the cable itself. However, activity can also be seen at the wall of the vial in which the test is conducted. This demonstrates that sonic activation will produce activity at the root canal wall.

Figure 5:
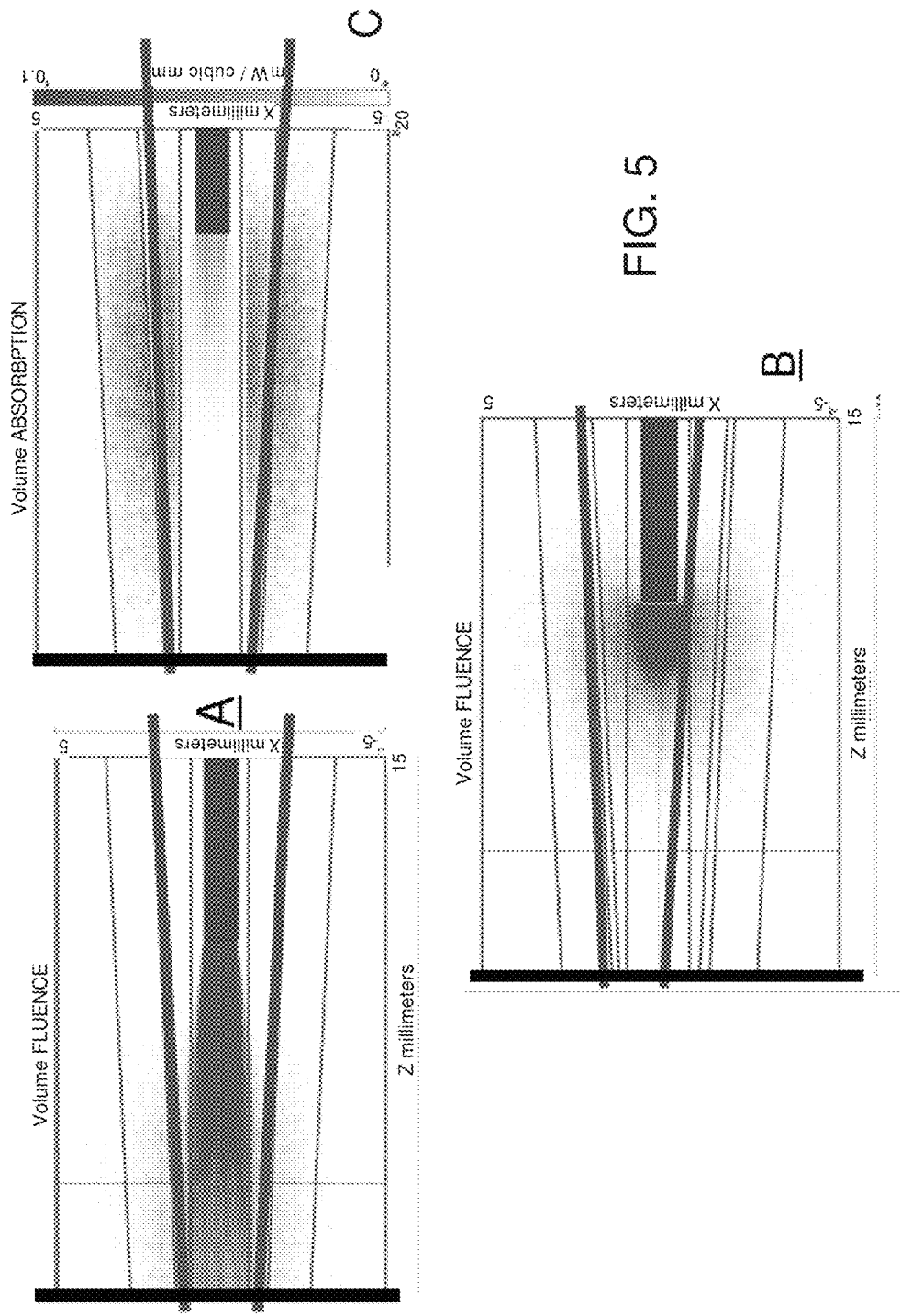
FIG. 5 contains images demonstrating the penetration of light from the fiber optic cable into the dentin due to activation of the micro-bubble solution.

Numerical modeling of the penetration of light into dentin is shown schematically in FIG. 5. In the schematics A-C of FIG. 5, the converging bold lines mark the edges of the dentin, and thus of the shaped canal. (Klein N, Kishen A, Foth H J. Root Canal Disinfection by Photodynamic Inactivation of Bacteria: Light Propagation in Root Canal, Gordon Research Conference on Lasers in Lasers in Medicine & Biology, Holderness, N H, Jul. 22-27, 2012). FIG. 5A schematically shows the penetration of light in a canal without the micro-bubble solution. As seen, the light emanating from the end of the fiber optic passes generally axially through the canal, and very little of the light even reaches the canal wall. FIG. 5B shows the canal with the micro-bubble solution. As seen, the light is scattered and reaches the canal walls. However, the light reaches the canal walls only in the vicinity of the end of the fiber optic cable. FIG. 5C shows the effect of activating the micro-bubble solution on light penetration. As seen, the light is scattered; it reaches axially well beyond the end of the fiber optic cable; and, the light penetrates well into the dentin to reach photosensitizing compound in the dentinal tubules and lateral canal. Because the light penetrates the dentin, the light will reach the photosensitive compound adhered to biofilm and bacteria within the dentin (i.e., in dentinal tubules) in addition to biofilm and bacteria in the main canal and lateral canals, to activate the photoactive compound within the dentinal tubules, lateral canals, and all other aspects of the root canal system.

Figure 6:
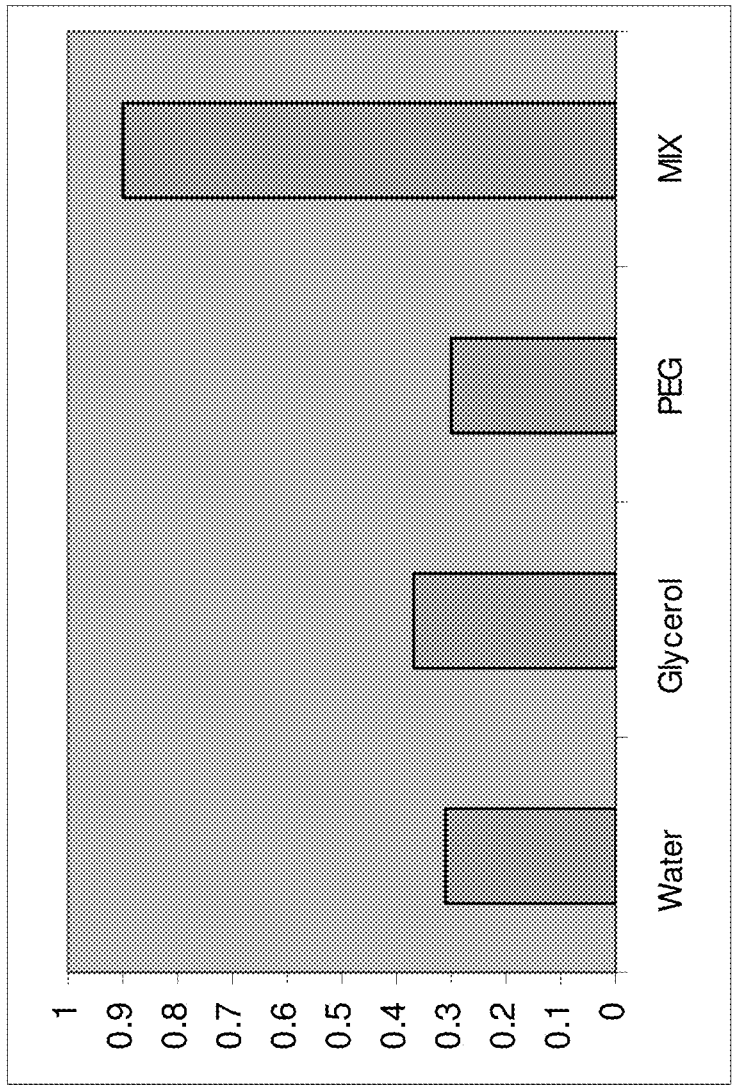
FIG. 6 is a graph comparing singlet oxygen release from methylene blue dissolved in (1) water, (2) glycerol, (3) polyethylene glycol and (4) a solution of water, glycerol and polyethylene glycol (MIX)
Figure 7:
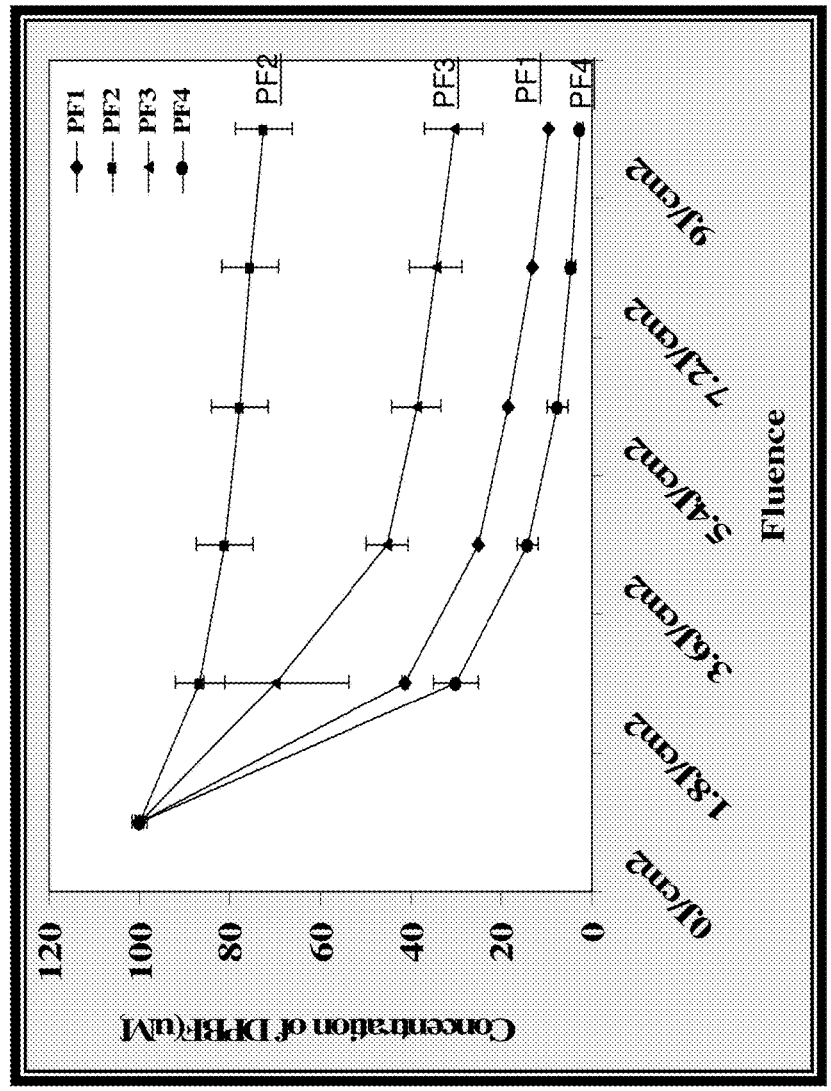

As noted above, when the light reaches the photosensitive compound, the photosensitive compound releases energy to convert the oxygen molecules to singlet oxygen. As noted above, $H_2O/Gly/PEG$ as the photosensitizing compound carrier solution substantially enhances the penetration of the photosensitizing compound into the dentin of the root canal. It also substantially increases the amount of oxygen singlet released. FIG. 6 is a chart showing the amount of singlet oxygen released during agitation of the micro-bubble solution in the root canal for four different carrier solutions: (1) water; (2) Glycerol, (3) PEG, and (4) a $H_2O/Gly/PEG$ mixture (MIX). The singlet oxygen release was measured using 1, 3-diphenylisobenzofuran (DPBF). DPBF is a chemical used to study the degree of release of singlet oxygen; it is not actually part of the micro-bubble solution or the photosensitizing solution. As is known, DPBF undergoes bleaching with singlet oxygen and this can be calorimetrically quantified. FIG. 7 shows increased concentration of DPBF, and thus increased concentration of oxygen singlets for varying photosensitizing solution formulations. In this test, four different photosensitizing formulations in micro-bubbles were tested for oxidation potential/singlet oxygen generation as follows:

Solution PF1 comprises 50 micro mol/L of MB in combination with perfluorodecahydronaphthalenel;

Solution PF2 comprises 50 micro mol/L of MB in combination with perfluorodecahydronaphthalene and $H_2O_2$ (66.6:33.3);

Solution PF3 comprises 50 micro mol/L of MB in an emulsion produced by mixing perfluorodecahydronaphthalene, $H_2O_2$, and Triton X-100 in the ratio 60:35:5; and Solution PF4 comprises 50 micro mol/L of MB in an emulsion produced by mixing perfluorodecahydronaphthalene, $H_2O_2$, and TritonX100 in the ratio 75:24.5:0.5.

It was found that with solution PF4 there was a significantly greater amount of singlet oxygen generation. Biofilm disruption is proportional to the amount of singlet oxygen released and/or the penetration of photosensitizer into the biofilm structure. Thus, the enhanced singlet oxygen generation lead to a better disruption of matured bacterial biofilm.

Importantly, the micro-bubble solution is mechanically (for example, sonically or ultrasonically) activated in the canal. This is to be compared with, for example, syringe irrigation. The fluid dynamics of syringe irrigation is shown schematically in FIG. 8. As shown, irrigation fluid is ejected from the end of the syringe. The flow of fluid adjacent the syringe is generally laminar. There is a small area of turbulent flow below the end of the syringe. However, due to the coronally directed reflux near the canal walls, much of this turbulence does not reach the canal wall. This results in a zone of active fluid circulation above the end of the syringe, and a zone of passive fluid circulation below the end of the syringe. Because of this, syringe irrigation does not induce significant stresses on the root canal wall. Therefore, solutions irrigated via syringe irrigation are not forced against the canal wall, and thus the irrigating solution will not penetrate very far into the dentin. Sonic and ultrasonic activation, on the other hand, produces lateral displacement of the fluid adjacent the tip, and causes fluid interaction with the canal wall. The graph of FIG. 9 shows the lateral penetration of sodium hypochlorite into the simulated lateral canals of root dentin and shows that sonic activation dramatically increases the number of lateral canals that are successfully penetrated. Similar synergistic effect is also observed with ultrasonic activation. It is observed that sonic activation of sodium hypochlorite with/without EDTA resulted in significant (numbers and magnitude) penetration into lateral canal.

Micro-Bubble Solution Dynamics

My disinfection method allows for the combination of the physical benefits of sonic agitation (physically displacing fluid/micro-bubbles towards the walls of the root canal) and the antibacterial effect of PDT (produced by singlet oxygen release). Larger and deeper penetration of singlet or reactive oxygen aids in marked elimination of biofilm bacteria.

When the micro-bubble solution is mechanically activated (sonically or ultrasonically) in the canal, both inertial (cavitational) and non-inertial bubble dynamics are produced in the canal. The inertial bubbles (which result from cavitation) will collapse and release energy resulting in heat and shear forces in the canal. These shear forces produce a hydrodynamic effect. The non-inertial (non-cavitational) bubbles oscillate in the fluid, and thus do not collapse, as do the inertial (cavitational) bubbles. These non-inertial bubbles move rapidly around mechanically activated files or tips and produce shear forces that are capable of dislodging materials (i.e., the biofilm) from the canal wall.

During sonic or ultrasonic activation of the micro-bubble solution, the gas cores of the bubbles expand during the rarefaction phase of the pressure wave and contracts during the compression phase. Enhanced micro-bubble/micro-bubble interaction also occurs during the ultrasonic/sonic activation of micro-bubble solution. This will increase the antibacterial effect of the photodynamic therapy. The higher antibacterial/anti-biofilm effect of photodynamic therapy is explained by the availability of oxygen carrier/oxidizing agent in the micro-bubbles and the activation energy supplied by the ultrasonic/sonic agitation. The above factors will lead to the marked production of singlet/reactive oxygen species, which are responsible for biofilm disruption, which is shown by the graphs of FIGS. 6 and 7.

The sonic or ultrasonic agitation/activation of the micro-bubble solution in the root canal results in the generation of anionic, stable and transient micro-bubbles. These micro-bubbles, during ultrasonic/sonic agitation, will yield improved micro-bubble/root canal wall interaction (physical effects of root canal disinfectant). It is known that the ultrasonic/sonic assisted irrigation produced the highest wall shear stress on the root canal wall and the highest turbulence intensity of fluid flow coronally from the ultrasonic/sonic tip. Thus the lateral movement of the micro-bubbles displayed has an important implication to enhance the physical effect of stable micro-bubbles to disrupt root canal biofilms.

FIG. 10 contains photomicrographs and a schematic drawing showing the micro-bubbles that are produced in a root canal upon sonic/ultrasonic activation of the micro-bubble solution in the canal. The oxidizing agent and the oxygen carrier, when activated, produce a significant amount of oxygen, which is released as the micro bubbles in the root canal. The micro-bubble interaction, as noted previously, enhances the photodynamic effect of the PDT. When the micro-bubble solution is mechanically activated, there is an interaction between the stable (anionic) bubbles and the canal wall. This micro-bubble/canal wall interaction generates electrostatic and physical/mechanical shear stresses which mechanically disrupt the biofilm. The mechanically activated micro-bubble solution thus 3-dimensionally improves the physical/mechanical effect within the root canal.

FIG. 11 contains graphs showing singlet oxygen yield of methylene blue (on the left hand graph) and rose bengal (on the right hand graph) both with sonic activation (square data points) and without sonic activation (diamond data points). The methylene blue graph (on the left hand side) shows that the initial absorbance of light is substantially higher when the micro-bubble solution is sonically activated. The absorbance of the light of the sonically activated micro-bubble solution then falls off much more rapidly than the absorbance of the solution without sonic activation. The rose bengal (RB) graph shows an absorbance level higher at all times for the test without sonic activation. However, as seen, in the sonically activated test, the absorbance fell off much more quickly than in the non-activated sample. The substantial fall off in absorbance in the sonically activated samples (as compared to the non-activated samples) for both the methylene blue and the rose bengal show substantial increase in micro-bubble activity within the first few seconds of activation of the micro-bubble solution. This thus demonstrates that the agitation enhances the singlet oxygen yield and subsequently the efficacy of photodynamic therapy.

Testing of Procedure

Often, testing is performed on immature (4-day old) biofilms. Immature, or young, biofilms are still soft, and can be easily removed. However, immature biofilms are rarely presented in an actual root canal procedure. In mature biofilms (i.e., 6 weeks old and older), the biofilm is calcified. The differences between the immature and mature biofilms can be seen in the photomicrographs of FIGS. 12 and 13.

FIG. 14 schematically demonstrates the strategy of my enhanced light activated disinfection method. The oxygen carrier ensures that there is a sufficient concentration of $O_2$ in the root canal, because there usually is little to no $O_2$ in a root canal. The oxidizer enhances the oxidation potential of the photosensitizing compound, and hence increases the number of oxygen singlets in the canal. In addition, the hydrogen peroxide in the micro-bubble solution (1) is activated by the low-energy level light and (2) will interact with organic debris within the root canal to form more free radicals which interact with gas within the micro-bubbles resulting in their growth and propulsion towards the root canal wall, as shown in FIGS. 24 and 25, in which the organic cell remnants are stained blue. Please note that the micro-bubbles expand to larger bubbles in proximity to organic remnants. This phenomenon allows the micro-bubbles to propel towards the organic materials. thereby facilitating debridement.

To test the effectiveness of the method, 50 single rooted teeth were initially sterilized and then incubated with *E. faecalis* in AC Broth, an all culture broth available from Sigma-Aldrich, for four weeks. The teeth were divided into five groups (with 10 teeth in each group) as follows:

Group 1: Control Group. In this group, the teeth received no disinfecting treatment.

Group 2: Traditional RCT. In this group, the teeth were subjected to shaping and cleaning. The teeth were shaped using Protaper® Universal files (available from Dentsply Tulsa Dental), and flushed with 6 ml of 5.25% sodium hypochlorite solution for 180 seconds.

Group 3: Conventional Light Activated Disinfection (LAD). In this group, the teeth were shaped with a Protaper® Universal file. The shaped canal was flushed with a 100 micro-molar solution of methylene blue in water for 300 seconds. The teeth were then subjected to light activation for 600 seconds without agitation. Light was introduced into the canal using the activator of FIG. 3, but without activating the activator.

Group 4: SAMP. In this group, the teeth were disinfected via my photo-chemically activated micro-bubble based root canal disinfection in which the micro-bubbles are pulsated and propelled toward the root canal wall by the activation energy. Initially the root canals of the teeth were shaped with Protaper® Universal files. The shaped canal was then flushed for 300 seconds with a 100 micro-molar solution of methylene blue dissolved in polyethylene glycol, glycerol and water. The PEG, ethanol and water were combined in a 30:20:50 ratio by volume. The excess photosensitive solution was removed from the canal using paper points. The canal was then filled with a micro-bubble solution comprised of PFC, $H_2O_2$, and Triton X-100 in a 75.0:24.5:0.5 ratio by volume. The micro-bubble solution was sonically activated for 180 seconds using an EndoActivator® driver fitted with a fiber optic cable, and the fiber optic cable delivered light from a diode laser (660 nm) into the canal of the micro-bubble solution with the introduction of light into the canal.

Group 5: RCT+SAMP—In this group, the teeth were shaped and cleaned in accordance with traditional RCT (as in Group 2) and were then subject to SAMP (as in Group 4).

After treatment, the teeth were cut axially to expose the canal of each tooth. Specimens of the root canal surface were taken and placed in Brain Heart Infusion (BHI) growth media to monitor the colony forming units. The samples were checked at four hours and again at twenty-four hours. In addition, the root canals were prepared from scanning electron microscopy.

FIG. 15 demonstrates the effectiveness of my disinfecting method. The first two columns of FIG. 15 contain images which show one week old bacterial biofilms of *Enterococcus faecalis* before and after treatment for the different groups. Each of the six images in the first two columns show active and dead bacteria, with the active bacteria being shown in green and the dead bacteria being shown in red. The two left-hand columns of FIG. 15 contains, images showing the three-dimensional confocal laser scanning microscopy reconstruction of the *Enterococcus faecalis* biofilms subjected to different treatments (60×). The left column shows the biofilm receiving no treatment (top), methylene blue (photosensitizer) (100 μmol/L) treatment (middle) and PF4 micro-bubble solution treatment (bottom). The middle column shows the biofilm subjected to light (660 nm) irradiation alone (top), methylene blue+light (660 nm) irradiation (middle) and PF4 micro-bubble solution treatment+light (660 nm). Finally, right-hand column shows the sagittal section of the treatment groups as described in the middle column MB. As seen in the top row, a significant amount of active (live) bacteria exists after just cleaning and shaping. Disinfection using sodium hypochlorite, as shown in the second row, kills (eliminates) nearly all of the active bacteria. However, there active bacteria remain. As shown in the bottom row, my photoenhanced activated micro-bubble based disinfection method eliminates virtually all of the active bacteria.

Experiments were conducted on 4 weeks old biofilm of *E. faecalis* grown with root canals of single rooted teeth. The results of the five different groups of teeth are summarized in Table I below.

TABLE I

EFFICACY OF BIOFILM DESTRUCTION

| Treatment groups | CFU ($\log_{10}$) after 4 hrs enrichment | No. of specimens positive after 24-hrs enrichment |
|---|---|---|
| Group 1: Control | 7.147 (±0.601) | 100% |
| Group 2: RCT (Instrumentation with Protaper ® F2 and sodium hypochlorite and EDTA irrigation) | 0.0 | 60% |
| Group 3: Conventional-LAD (After instrumentation, methylene blue 80 micro molar solution was used to photosensitized and light activation (36J)) | 5.639 (±0.066) | 100% |
| Group 4: SAMP (After instrumentation, photosensitized with MB (5 | 0.0 | 0% |

TABLE I-continued

EFFICACY OF BIOFILM DESTRUCTION

| Treatment groups | CFU ($\log_{10}$) after 4 hrs enrichment | No. of specimens positive after 24-hrs enrichment |
|---|---|---|
| min) and micro-bubbles were added and sonically activated with EndoActivator ® driver for 5 min | | |
| Group 5: RCT + SAMP (combination of steps in groups 2 and 4) | 0.0 | 0% |

The root samples were split into two halves. One half of the root was used for microbiological culture analysis (shown above) and described just below, and the other half was used for SEM analysis described below in conjunction with FIGS. 16-19. Eight tooth samples were used for microbiological culture analysis while four samples were used for SEM analysis under each group.

As seen, the control (Group 1) and conventional-LAD (Group 3) samples both had a significant number of colony forming units (CFU's) of active bacteria after four hours of enrichment in a growth media, and all of the samples of these two groups tested positive for colony forming units after 24 hours. In Group 2, where samples were treated via traditional root canal therapy (RCT), there were no colony forming units after four hours of enrichment in growth media. However, 60% of the Group 2 (RCT treated) samples had colony forming units after 24 hours in the growth/enrichment media. This is to be compared with the teeth of Groups 4 and 5 which were treated via SAMP and RCT+SAMP, respectively, as described above. In both on these groups, there were no colony forming units in the growth/enrichment media after four hours, and importantly, there were no colony forming units in the growth media after 24 hours. The 24 hour test demonstrates that the SAMP and RCT+SAMP treatment substantially destroyed all the bacteria in the canals. The teeth from Group 4 (SAMP alone) demonstrate that SAMP is highly effective, and the chemical disinfection used in traditional RCT need not be used if the canal is disinfected via my SAMP method.

FIGS. 16-19 contain scanning electron photomicrographs of the treated root canals of teeth from Groups 1, 3 (two variations) and 4. FIG. 16 contains photomicrographs of a tooth from Group 1 (control). As seen, the biofilm is still present. FIG. 17 contains photomicrographs of a tooth from Group 3 (PDT with MB in water without activation). As seen, there is some disruption of the biofilm, but the biofilm is still, in large measure, present on the root canal surface. FIG. 18 demonstrates the effect of the micro-bubble solution on conventional light activated disinfection (LAD). As seen, the biofilm is disrupted to a greater extent than in the photomicrographs of FIG. 17. However, the biofilm is still present. FIG. 18 contains photomicrographs of a tooth from Group 4 (SAMP). As seen, in the teeth treated via sonically activated micro-bubble based photodynamic therapy, the biofilm is fully removed, the canal wall can be clearly seen, and the dentinal tubules are opened.

FIGS. 20-22 contain color-enhanced images of a root canal comparing a control tooth with root canals treated via photoactivation of methylene blue in water in the presence of activated micro-bubble solution and photoactivation of methylene blue in water, ethanol and polyethylene glycol in the presence of activated micro-bubble solution, to demonstrate the effectiveness of the water/alcohol/PEG carrier solution. In these photographs, active bacteria are shown in green and dead bacteria as shown in red. FIG. 20 contains photomicrographs of a control tooth. These pictures show a significant amount of active bacteria (in green). The control biofilms show multilayered biofilm structure of more than 45 microns thickness adherent to the root dentin substrate FIG. 21 contains photomicrographs of a tooth treated with MB in a water carrier and then subject to sonic and light activation of the micro-bubble solution; and FIG. 22 contains photomicrographs of a tooth treated with MB in the polyethylene glycol, alcohol and water carrier solution, and then subject to sonic and light activation of the micro-bubble solution. Both FIGS. 21 and 22 show that substantially all of the active bacteria have been eliminated. These two figures also show that effect of the micro-bubble solution. Although use of the polyethylene glycol-alcohol-water carrier solution for the MB allows for better penetration of the MB into the dentin, the sonic and light activation of the micro-bubble solution compensates for this, and in both groups (FIGS. 21 and 22), the biofilm is substantially completely disrupted. Dead bacteria are noted even within the dentinal tubules.

The images in FIGS. 24 and 25 were obtained by interactive cell components in serum albumin mixed with micro-bubbles and observing the interaction under light microscopy. These images highlight the micro-bubble dynamics even without photoactivation.

As can be seen from the foregoing, dissolving of a photoactive compound in a water/alcohol solution enables the photosensitizing compound (i.e., the methylene blue) to better penetrate the dentinal tubules and anatomical complexities of the root canal. Further, the utilization of the micro-bubble solution produces a greater degree (more than 3×) of reactive oxygen (i.e., oxygen singlets), allows for better penetration of light into the dentin, improves the physical/mechanical effects of the micro-bubbles (pulsating/propelling), and thus increases the anti-biofilm efficacy of PDT. My enhanced micro-bubble based light activated disinfection disrupts and substantially eliminates the biofilm from the root canal system, and even in uninstrumented portions of the root canal. Thus, the disclosed method provides for a substantially better disinfection of the root canal than has been obtained with standard or conventional root canal treatment. This better disinfection of the canal allows for better results, and should result in fewer retreatments. Further, because uninstrumented portions of the canal are disinfected, SAMP allows for effective MIE.

As various changes could be made in the above constructions without departing from the scope of the invention, it is intended that all matter contained in the above description or shown in the accompanying drawings shall be interpreted as illustrative and not in a limiting sense.

The invention claimed is:

1. A method of disinfecting a root canal during endodontic treatment comprising:
   a) introducing a photoactive solution into the root canal, the photoactive solution containing a photoactive compound dissolved in an alcohol carrier solution;
   b) removing excess photoactive solution from the root canal after the photoactive compound has been allowed to penetrate dentinal tubules and anatomical complexities of the root canal such that the photoactive compound adheres to biofilm and bacteria in the root canal;
   c) introducing a micro-bubble solution into the root canal after said step of removing excess photoactive solution has been completed; said micro-bubble solution being comprised of at least one oxygen carrier, at least one oxidizing agent, and at least one surfactant;

d) activating the micro-bubble solution in the root canal to generate micro-bubbles of oxygen molecules in the root canal; said micro-bubbles having a stabilizing shell formed from said at least one surfactant; whereby said micro-bubbles mechanically disrupt the biofilm and remove debris and smear layer from a wall of the root canal; and e) after the micro-bubble solution has been introduced into the root canal, introducing light into the root canal by means of a light transmitting probe to activate the photoactive compound, the activated photoactive compound releasing energy to convert the oxygen molecules to singlet oxygen which reacts with the biofilm and bacteria in the root canal to destroy the biofilm and bacteria.

2. The method according to claim 1 wherein the steps of activating the micro-bubble solution and introducing light into the root canal to activate the photoactive compound are performed simultaneously.

3. The method according to claim 1 wherein the step of introducing the photoactive solution into the root canal comprises flushing the root canal with the photoactive solution.

4. The method according to claim 1 wherein the step of removing excess photoactive solution is performed after the root canal has been exposed to the photoactive solution for at least about 60 seconds.

5. The method according to claim 1 wherein the step of removing excess photoactive solution is performed after the root canal has been exposed to the photoactive solution for about 60 seconds to about 180 seconds.

6. The method according to claim 1 wherein the micro-bubble solution is activated in the root canal for at least about 60 seconds.

7. The method according to claim 1 wherein the micro-bubble solution is activated in the root canal for about 60 seconds to about 180 seconds.

8. The method according to claim 1 wherein the light is from a halogen lamp, an LED or a laser.

9. The method according to claim 8 wherein the light is from a laser, the laser being matched according to the photoactive compound used.

10. The method of claim 9 wherein the photoactive compound is methylene blue, and the laser operates at 660 nm.

11. The method according to claim 1 wherein the photoactive compound is chosen from the group consisting of toluidine blue (TBO), methylene blue (MB), rose bengal (RB), arianor steel blue, tryptan blue, crystal violet, azure blue cert, azure B chloride, azure 2, azure A chloride, azure B tetrafluoroborate, thionin, azure A eosinate, azure B eosinate, azure mix sicc, azure II eosinate, haematoporphyrin HCl, haematoporphyrin ester, aluminum disulphonated phthalocyanine, chlorins, photoactive fullerenes (e.g. CI6-b), aminolevulinic acid (ALA), bacteriochlorins, phthalocyanines, pheophorbides, purpurins, naphthalocyanines, indocyanine green, and combinations thereof.

12. The method according to claim 1 wherein the photoactive compound is methylene blue or rosen bengal arianor steel blue.

13. The method according to claim 1 wherein the photoactive compound is methylene blue.

14. The method according to claim 1 wherein the alcohol carrier solution comprises polyethylene glycol and/or ethanol.

15. The method according to claim 1 wherein the alcohol carrier solution comprises polyethylene glycol, ethanol, and water.

16. The method according to claim 14 wherein the polyethylene glycol is glycerol.

17. The method according to claim 15 wherein the polyethylene glycol, ethanol, and water are mixed in a ratio such as to have a refractive index close to that of dentin and to be able to penetrate into the dentinal tubules.

18. The method according to claim 15 wherein the polyethylene glycol, ethanol, and water are combined in a ratio of about 1:1:1 to about 3:1:2 by volume.

19. The method according to claim 15 wherein the polyethylene glycol, ethanol, and water are combined in a ratio of about 3:2:5 by volume.

20. The method according to claim 1 wherein the photoactive compound has a concentration of about 2 micro molar to about 100 micro molar in the photoactive solution.

21. The method according to any of claim 1 wherein the photoactive compound has a concentration of about 100 micro molar in the photoactive solution.

22. The method according to claim 1 wherein the at least one oxygen carrier of the micro-bubble solution is chosen from the group consisting of perfluorodecahydro naphthalene, perfluorodecalin, perfluorohexane, octafluoropropane, perfluorobutane, perfluorooctane, perfluoromethyldecalin and $O_2IrCl(CO)P[C_6H_5]_3)_2$, and combinations thereof.

23. The method according to claim 1 wherein the at least one oxygen carrier of the micro-bubble solution is a perflourocarbon.

24. The method according to claim 1 wherein the at least one oxidizing agent of the micro-bubble solution is chosen from the group consisting of hydrogen peroxide ($H_2O_2$), dilute sodium hypochlorite, dimethyl sulfoxide and chlorine dioxide and combinations thereof.

25. The method according to claim 1 wherein the at least one oxidizing agent of the micro-bubble solution is of hydrogen peroxide ($H_2O_2$).

26. The method according to claim 25 wherein the hydrogen peroxide ($H_2O_2$) has a concentration of about 3% to about 40% $H_2O_2$.

27. The method according to claim 25 wherein the hydrogen peroxide ($H_2O_2$) has a concentration of about 35% $H_2O_2$.

28. The method according to claim 1 wherein the at least one surfactant of the micro-bubble solution is chosen from the group consisting of mineral oil, glycerol, polyethylene glycol, non-ionic detergent, polypropylene glycol, SDS, a nonionic polyoxyethylene surfactant, cetrimide (an antibacterial detergent), and combinations thereof.

29. The method according to claim 1 wherein the at least one surfactant of the micro-bubble solution is a nonionic polyoxyethylene surfactant.

30. The method according to claim 1 wherein the at least one oxygen carrier, the at least one oxidizing agent and the at least one surfactant of the micro-bubble solution are combined in a ratio of about 73:26.5:0.5 to about 75:24:1 by volume.

31. The method according claim 1 wherein the at least one oxygen carrier, the at least one oxidizing agent and the at least one surfactant of the micro-bubble solution are combined in a ratio of 75:24.5:0.5 by volume.

32. The method of claim 1 wherein said step of activating the micro-bubble solution comprises mechanically activating the micro-bubble solution.

33. The method of claim 1 wherein said step of activating the micro-bubble solution comprises sonically or ultrasonically activating the micro-bubble solution.

34. The method according to claim 1 wherein the at least one surfactant of the micro-bubble solution has antimicrobial properties.

\* \* \* \* \*